(12) United States Patent
Baroud

(10) Patent No.: US 8,409,211 B2
(45) Date of Patent: Apr. 2, 2013

(54) INTEGRATED CEMENT DELIVERY SYSTEM FOR BONE AUGMENTATION PROCEDURES AND METHODS

(75) Inventor: Gamal Baroud, Canton-de Hatley (CA)

(73) Assignee: Societe de Commercialisation des Produits de la Recherche Appliquee Socpra Sciences et Genie S.E.C. (CA)

( * ) Notice: Subject to any disclaimer, the term of this patent is extended or adjusted under 35 U.S.C. 154(b) by 1174 days.

(21) Appl. No.: 12/246,798

(22) Filed: Oct. 7, 2008

(65) Prior Publication Data

US 2009/0093818 A1  Apr. 9, 2009

Related U.S. Application Data

(63) Continuation-in-part of application No. PCT/CA2007/000579, filed on Apr. 5, 2007.

(60) Provisional application No. 60/789,891, filed on Apr. 7, 2006.

(51) Int. Cl.
*A61B 17/58* (2006.01)
(52) U.S. Cl. ............................................ 606/93; 606/92
(58) Field of Classification Search .............. 606/92–95; 604/57, 58, 103.01, 264
See application file for complete search history.

(56) References Cited

U.S. PATENT DOCUMENTS

| | | |
|---|---|---|
| 1,988,480 A | 1/1935 | Campkin |
| 2,602,446 A | 7/1952 | Glass et al. |
| 2,627,270 A | 2/1953 | Glass |
| 2,690,178 A | 9/1954 | Bickford |
| 2,702,547 A | 2/1955 | Glass |
| 3,365,936 A | 1/1968 | Hubin et al. |
| 3,623,474 A | 11/1971 | Hellman et al. |
| 3,631,847 A | 1/1972 | Hobbs, II |
| 3,701,345 A | 10/1972 | Hellman et al. |
| 4,099,528 A | 7/1978 | Sorenson et al. |
| 4,180,068 A | 12/1979 | Jacobson et al. |
| 4,202,332 A | 5/1980 | Tersteegen et al. |
| 4,236,109 A | 11/1980 | Ingle, Jr. |
| 4,294,251 A | 10/1981 | Greenwald et al. |
| 4,399,100 A | 8/1983 | Zsolnay et al. |
| 4,423,371 A | 12/1983 | Senturia et al. |
| 4,884,573 A | 12/1989 | Wijay et al. |
| 4,891,591 A | 1/1990 | Johnston et al. |

(Continued)

FOREIGN PATENT DOCUMENTS

| | | |
|---|---|---|
| CA | 2524140 | 12/2003 |
| CA | 2545436 | 1/2005 |

(Continued)

OTHER PUBLICATIONS

European Search Report EP 07 71 9509; Jun. 1, 2010.

*Primary Examiner* — Kevin T Truong
*Assistant Examiner* — Christian Sevilla
(74) *Attorney, Agent, or Firm* — Cantor Colburn LLP

(57) ABSTRACT

A cement delivery system for vertebroplasty including a rigid cannula having a tubular inner wall defining a central conduit to deliver bone cement and a tubular outer wall extending around the inner wall and spaced apart therefrom to define a peripheral conduit for aspirating bone fluids. Aspirating means communicate with a proximal outlet port of the peripheral conduit to create a pressure gradient between the central conduit and the peripheral conduit to provide a hydraulic force guiding the displacement of bone fluid and the flow of cement. Also, a bone cement delivery system including a rigid cannula having a tubular inner wall defining a central conduit, a tubular outer wall extending around the inner wall and spaced apart therefrom to define a peripheral conduit, and a tubular middle wall extending between the inner and peripheral walls and spaced apart therefrom to define a middle conduit around the central conduit.

9 Claims, 20 Drawing Sheets

U.S. PATENT DOCUMENTS

| | | | |
|---|---|---|---|
| 4,952,205 A | 8/1990 | Mauerer et al. | |
| 5,007,904 A | 4/1991 | Densmore et al. | |
| 5,012,818 A | 5/1991 | Joishy | |
| 5,108,404 A | 4/1992 | Scholten et al. | |
| 5,145,250 A | 9/1992 | Planck et al. | |
| 5,211,477 A | 5/1993 | Li | |
| 5,279,149 A | 1/1994 | Williams et al. | |
| 5,436,565 A | 7/1995 | Gammell | |
| 5,681,286 A | 10/1997 | Niehoff | |
| 5,681,317 A | 10/1997 | Caldarise | |
| 5,685,821 A * | 11/1997 | Pike | 600/118 |
| 5,718,678 A * | 2/1998 | Fleming, III | 604/43 |
| 5,800,439 A * | 9/1998 | Clyburn | 606/94 |
| 5,872,447 A | 2/1999 | Hager, III | |
| 5,898,309 A | 4/1999 | Becker et al. | |
| 5,947,929 A | 9/1999 | Trull | |
| 6,066,154 A * | 5/2000 | Reiley et al. | 606/192 |
| 6,179,569 B1 | 1/2001 | Kojima et al. | |
| 6,241,734 B1 | 6/2001 | Scribner et al. | |
| 6,348,055 B1 | 2/2002 | Preissman | |
| 6,368,307 B1 | 4/2002 | Ziemba et al. | |
| 6,575,936 B1 | 6/2003 | Kojima et al. | |
| 6,613,054 B2 | 9/2003 | Scribner et al. | |
| 6,958,053 B1 | 10/2005 | Reilly | |
| 6,979,352 B2 | 12/2005 | Reynolds | |
| 7,008,433 B2 | 3/2006 | Voellmicke et al. | |
| 7,112,205 B2 | 9/2006 | Carrison | |
| 7,153,307 B2 | 12/2006 | Scribner et al. | |
| 7,226,481 B2 | 6/2007 | Kuslich | |
| 7,465,290 B2 | 12/2008 | Reilly | |
| 7,549,977 B2 | 6/2009 | Schriver et al. | |
| 7,563,249 B2 | 7/2009 | Schriver et al. | |
| 7,572,263 B2 | 8/2009 | Preissman | |
| 7,662,133 B2 | 2/2010 | Scarberough et al. | |
| 2001/0049531 A1 | 12/2001 | Reiley et al. | |
| 2002/0058947 A1 * | 5/2002 | Hochschuler et al. | 606/94 |
| 2002/0173796 A1 | 11/2002 | Cragg | |
| 2004/0260303 A1 | 12/2004 | Carrison | |
| 2005/0070915 A1 | 3/2005 | Mazzuca et al. | |
| 2005/0113843 A1 | 5/2005 | Arramon | |
| 2005/0131390 A1 * | 6/2005 | Heinrich et al. | 606/1 |
| 2005/0177111 A1 | 8/2005 | Ozeri et al. | |
| 2005/0234498 A1 | 10/2005 | Gronemeyer et al. | |
| 2006/0074433 A1 | 4/2006 | McGill et al. | |
| 2006/0079905 A1 | 4/2006 | Beyar et al. | |
| 2006/0089655 A1 | 4/2006 | Watkins et al. | |
| 2006/0122621 A1 | 6/2006 | Truckai et al. | |
| 2006/0122624 A1 | 6/2006 | Truckai et al. | |
| 2006/0149379 A1 | 7/2006 | Kuslich et al. | |
| 2007/0027230 A1 | 2/2007 | Beyar et al. | |
| 2007/0032567 A1 | 2/2007 | Beyar et al. | |
| 2007/0118144 A1 | 5/2007 | Truckai et al. | |
| 2007/0191858 A1 | 8/2007 | Truckai et al. | |
| 2007/0198024 A1 | 8/2007 | Plishka et al. | |
| 2008/0065089 A1 | 3/2008 | Osorio et al. | |
| 2008/0119821 A1 | 5/2008 | Agnihotri et al. | |
| 2008/0195114 A1 | 8/2008 | Murphy | |
| 2008/0249530 A1 | 10/2008 | Truckai et al. | |

FOREIGN PATENT DOCUMENTS

| | | |
|---|---|---|
| CA | 2575699 | 2/2006 |
| CA | 2603010 | 10/2006 |
| CA | 2603010 | 3/2010 |
| DE | 100 08 481 A 1 | 9/2001 |
| DE | 102004043294 | 3/2006 |
| FR | 2819714 | 7/2002 |
| WO | 02/00143 | 1/2002 |
| WO | 02100282 | 12/2002 |
| WO | 2006/062939 | 6/2006 |

* cited by examiner

FIG_1

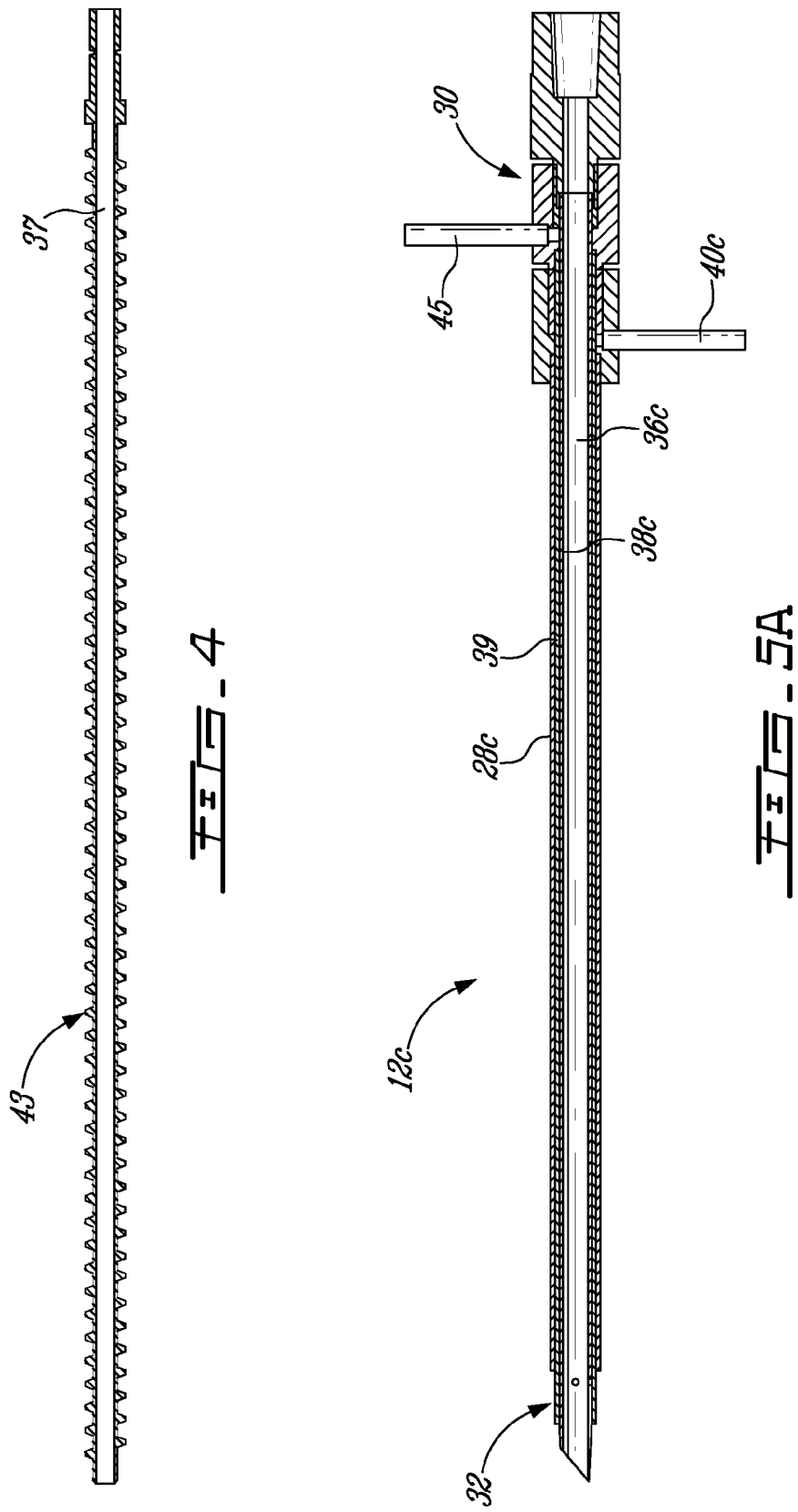

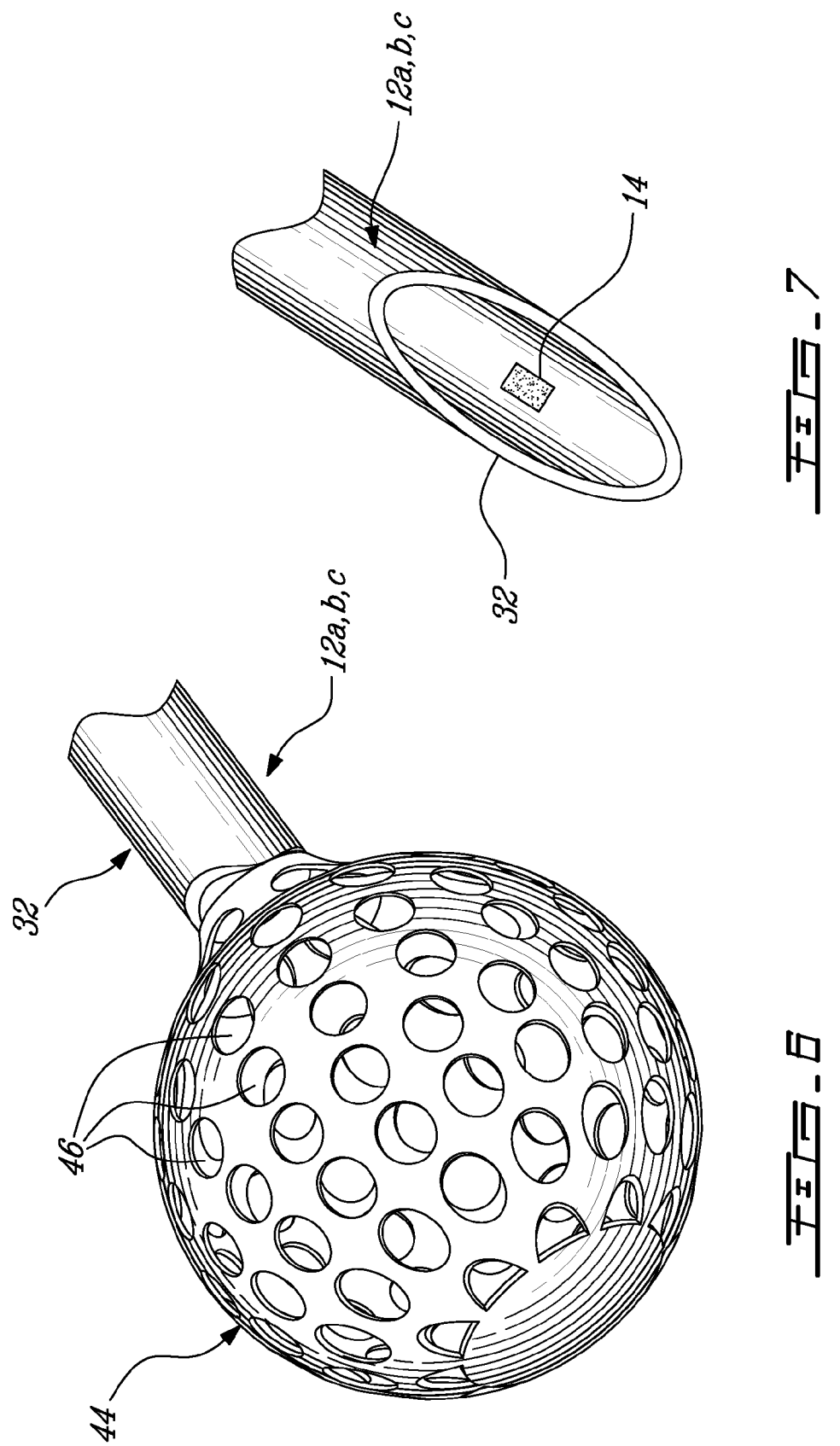

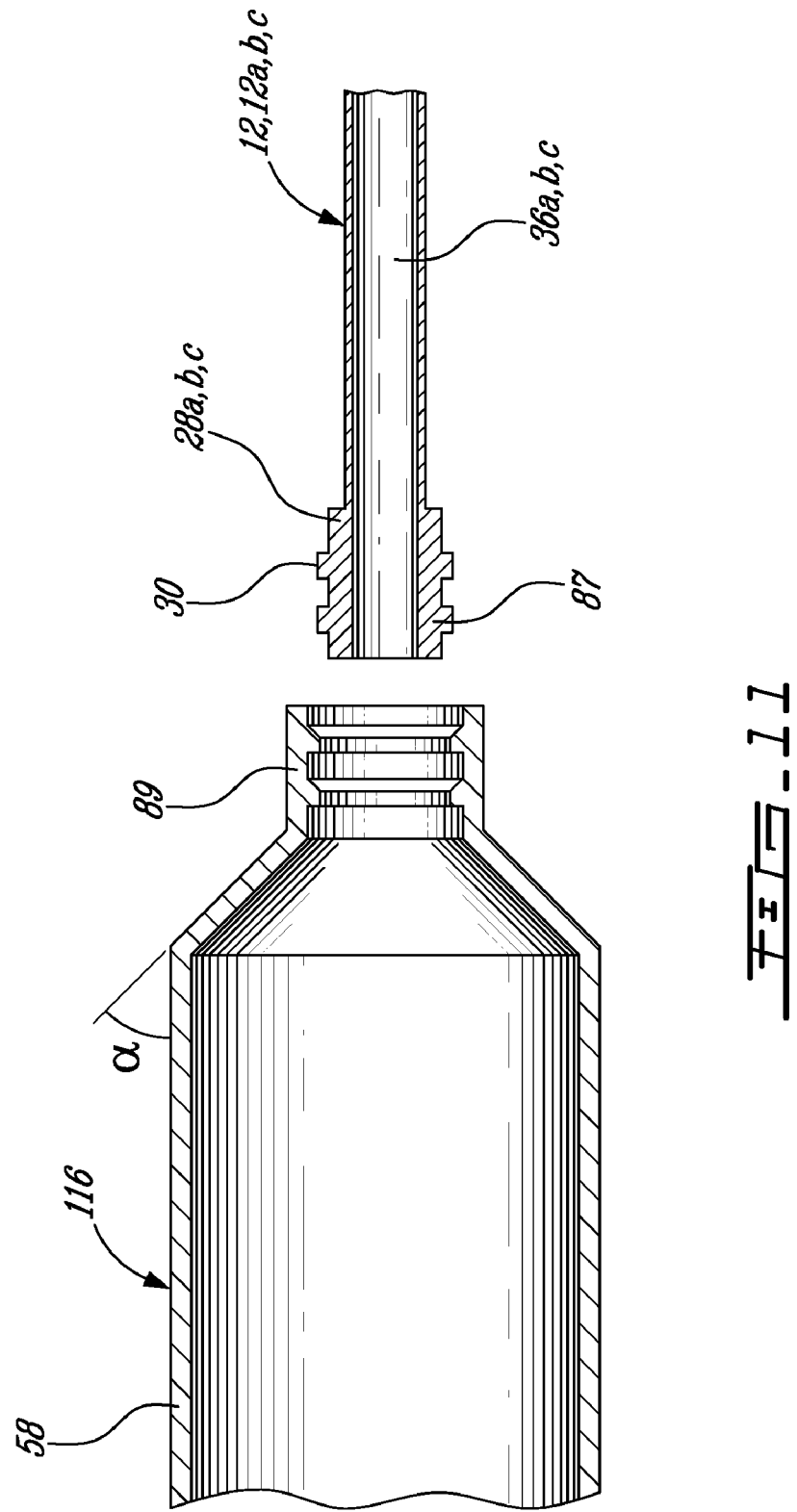

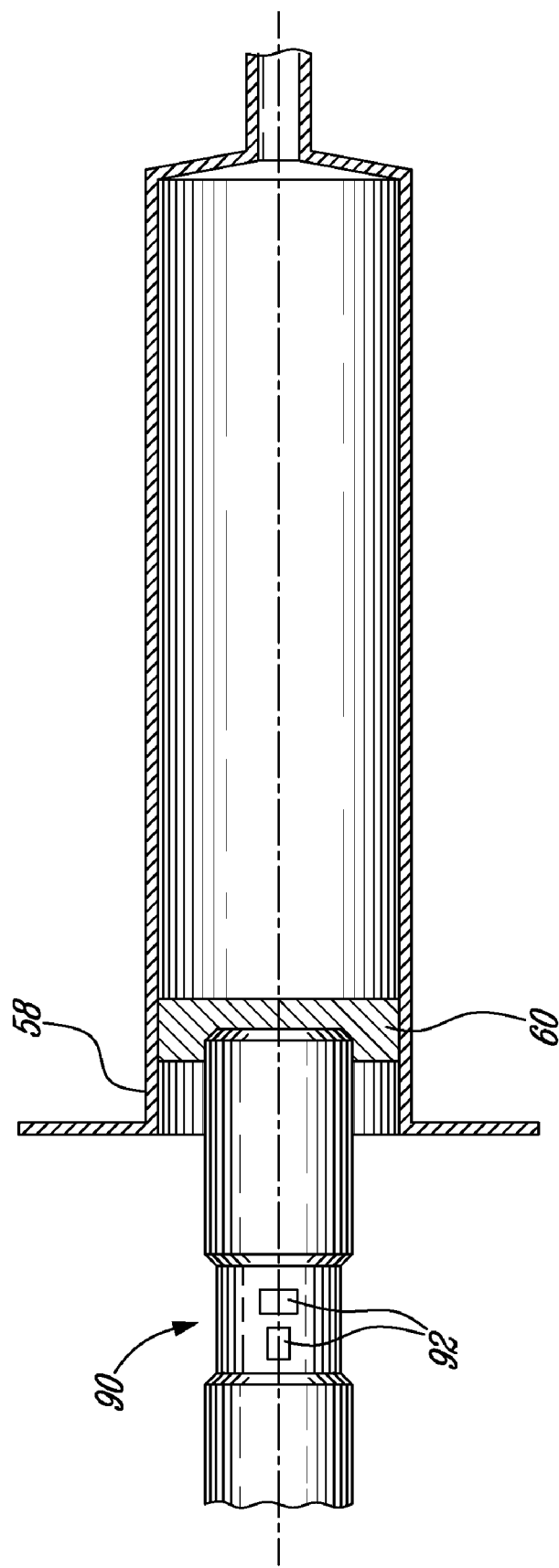

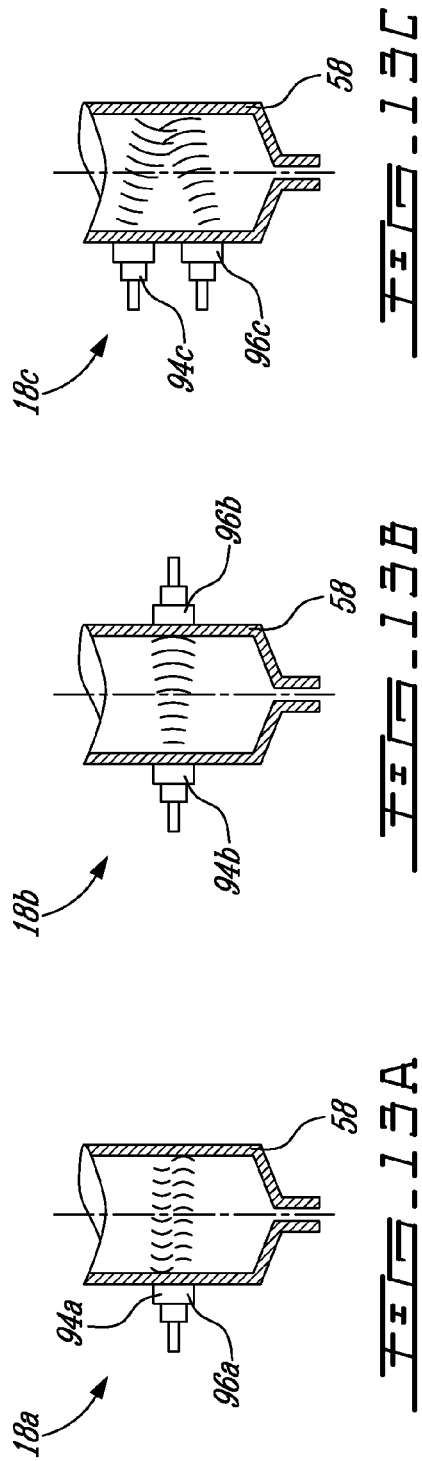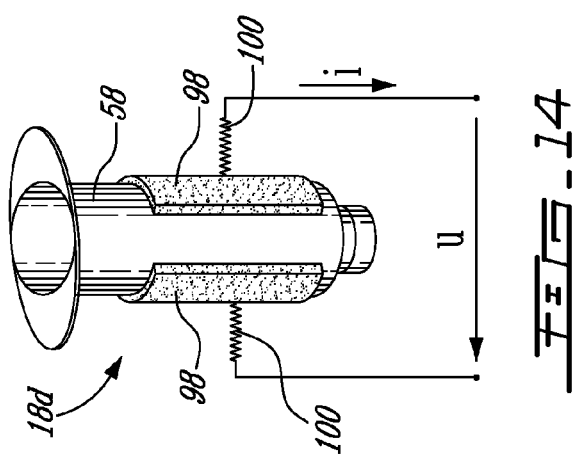

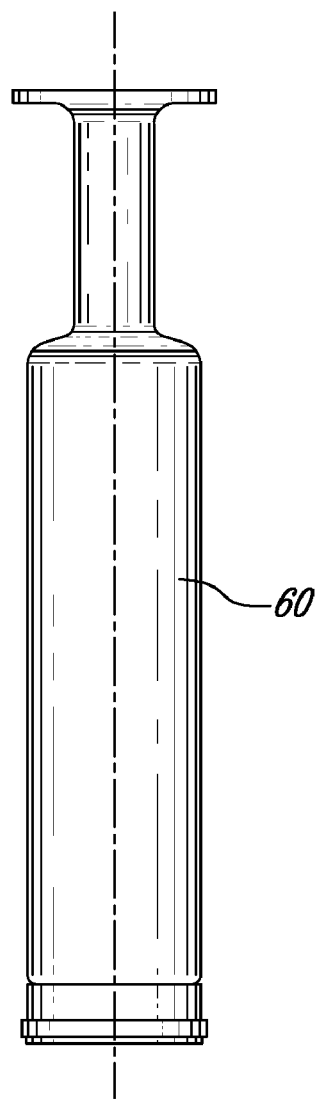
FIG_15A
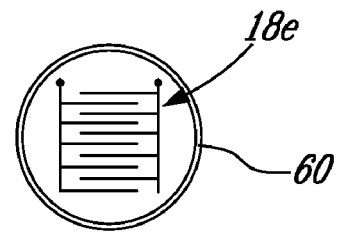
FIG_15B

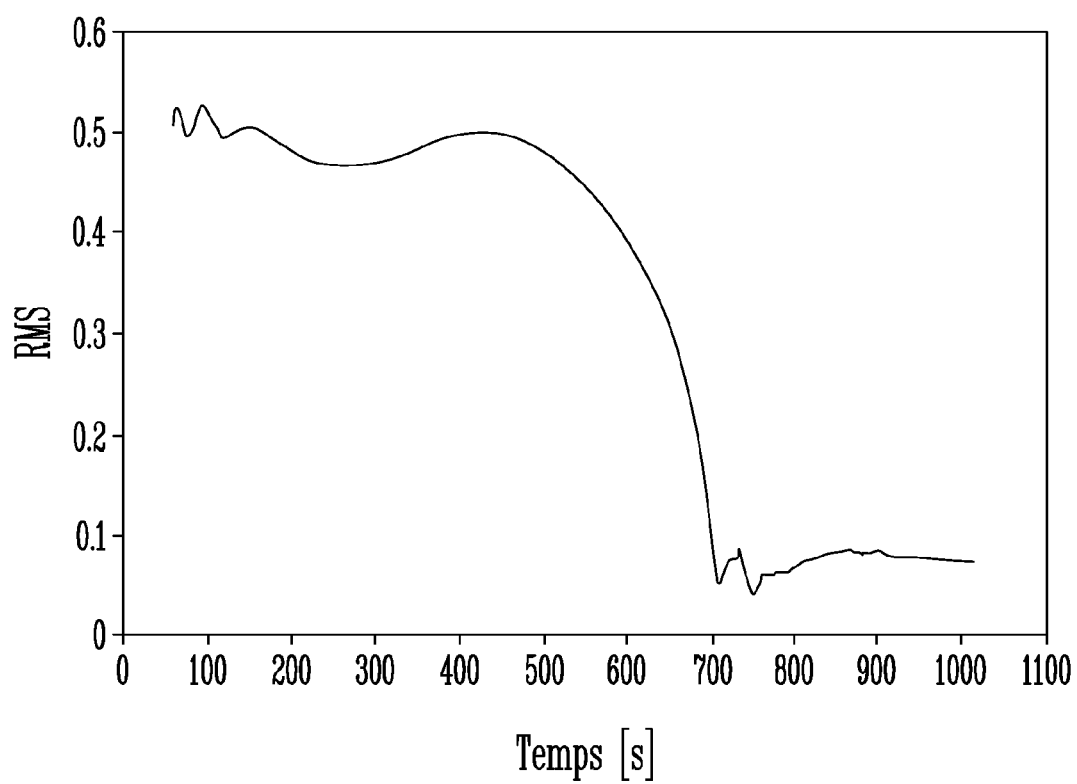
FIG_16

FIG_21

FIG_22

INTEGRATED CEMENT DELIVERY SYSTEM FOR BONE AUGMENTATION PROCEDURES AND METHODS

CROSS-REFERENCE TO RELATED APPLICATIONS

This application is a continuation-in-part of PCT Patent Application No. CA2007/000579 filed Apr. 5, 2007, which claims priority on U.S. Provisional Patent Application No. 60/789,891 filed Apr. 7, 2006, both of which are incorporated by reference.

FIELD OF THE INVENTION

The present invention relates to an apparatus for performing bone augmentation procedures, and more particularly to a cement delivery system for such procedures and to a method for the use of such a system.

BACKGROUND ART

A number of different types of bone cement injection procedures are routinely practiced, among which is vertebroplasty.

Unfortunately, the pressure required to inject cement can easily reach values beyond human physical limit. A number of pressure-controlled devices are available to increasing the pressure applied to the cement for delivery, however such devices may increase the risk of cement leakage because of a lack of control on the cement flow rate. It is also known to lower the cement viscosity to ease the injection, however such an approach may also generally increase the risk of cement leakage.

While most cement leaks are inconsequential, every leak nevertheless exposes patients to serious risks, such as spinal cord and nerve root compression, pulmonary embolism, and possibly even death.

Further, the viscosity of the bone cement changes as the cement polymerizes, while also varying substantially due to various factors such as environmental conditions (e.g. temperature, humidity), the mixing technique used, as well as the batch and type of cement used. Physicians often use suggestive methods such as visual and/or tactile inspection to evaluate whether the viscosity of cement is adequate for injection, such methods being generally imprecise and not easily reproducible.

Accordingly, improvements are desirable.

SUMMARY OF INVENTION

In accordance with the present invention, there is provided a bone cement delivery system for vertebroplasty comprising a rigid cannula having a tubular inner wall defining and surrounding a central conduit to deliver bone cement into a vertebra under pressure, the inner wall defining a distal outlet port of the central conduit at a distal end of the cannula, a tubular outer wall extending around the inner wall and spaced apart therefrom to define a peripheral conduit around the central conduit for aspirating bone fluids, the outer wall defining a distal inlet port of the peripheral conduit at the distal end of the cannula, the outer wall having an outer diameter not exceeding acceptable parameters for vertebroplasty, a proximal end of the cannula including a proximal inlet port in communication with the central conduit and a proximal outlet port in communication with the peripheral conduit, and aspirating means communicating with the proximal outlet port of the peripheral conduit to create a pressure gradient between the central conduit and the peripheral conduit to provide a hydraulic force guiding the displacement of bone fluid and the flow of cement.

Also in accordance with the present invention, there is provided a bone cement delivery system comprising a rigid cannula having a tubular inner wall defining and surrounding a central conduit for bone cement delivery, the inner wall defining a distal outlet of the central conduit at a distal end of the cannula, a tubular outer wall extending around the inner wall and spaced apart therefrom to define a peripheral conduit around the central conduit, the outer wall defining a distal inlet of the peripheral conduit at the distal end of the cannula, and a proximal end of the cannula including a proximal inlet port in communication with the central conduit and a proximal outlet port in communication with the peripheral conduit, and further comprising a tubular middle wall extending between the inner and peripheral walls and spaced apart therefrom to define a middle conduit around the central conduit, the peripheral conduit being defined around the middle conduit.

Also in accordance with the present invention, there is provided a medical cannula comprising at least one tubular wall defining and surrounding an injection conduit, the wall defining a distal outlet of the injection conduit at a distal end of the cannula, and a proximal end of the cannula including a proximal inlet in communication with the injection conduit, and an elastic and permeable membrane covering the distal outlet of the injection conduit for delivery of injected fluid therethrough.

Also in accordance with the present invention, there is provided a method of injecting bone cement within a vertebra, comprising injecting bone cement within the vertebra through a pedicle, and at least one of aspirating bone fluid from the vertebra through said pedicle simultaneously with the bone cement injection and creating a pressure gradient between the injection and aspiration steps to provide a hydraulic force guiding the displacement of bone fluid and the flow of bone cement.

Also in accordance with the present invention, there is provided a bone cement delivery device, comprising a syringe body for containing the bone cement, a plunger snuggly and slidably received within the syringe body for pushing the bone cement out of the syringe body, a driving system connected to the plunger and sliding the plunger within the syringe body, and a control system controlling the driving system in a displacement-controlled and continuous manner over a given time period to produce a constant flow of bone cement out of the syringe body within the time period based on commands from a user.

Also in accordance with the present invention, there is provided a bone cement delivery device comprising a body for containing the bone cement therein and for progressively injecting the bone cement therefrom for delivery into the bone, at least one sensor for measuring a physical parameter of the bone cement within the body, wherein the sensor is integral with the body, the at least one parameter being indicative of curing of the bone cement, and a display unit receiving data from the sensor and displaying at least one of the physical parameter and the curing progress of the bone cement.

Also in accordance with the present invention, there is provided a method of injecting bone cement within a bone, comprising monitoring at least one parameter indicative of a curing of the bone cement directly within a bone cement delivery device, and injecting the bone cement in the bone with the delivery device based on the at least one parameter.

Also in accordance with the present invention, there is provided a control system for a bone cement delivery device, the control system comprising a delivery pressure sensor for measuring a cement delivery pressure and producing corresponding delivery pressure data, a control panel for receiving commands from a user and producing corresponding command data, a driving system for actuating the cement delivery device to deliver the bone cement, a control module for receiving the command data and the delivery pressure data, and for sending a control signal actuating the driving system based on the command data and the delivery pressure data such as to deliver the bone cement in a steady flow, and a display unit for receiving the pressure data from the control module and displaying delivery pressure information based on the delivery pressure data.

Also in accordance with the present invention, there is provided an integrated cement delivery system comprising a cement delivery device including a syringe body for containing the bone cement, a plunger slidably received within the syringe body for pushing the bone cement out of the syringe body, and a driving system connected to the plunger and sliding the plunger within the syringe body, an injection pressure sensor measuring an injection pressure of the cement within the syringe body, a control system controlling the driving system in a displacement-controlled and continuous manner to produce a steady flow of bone cement out of the syringe body based on data from the injection pressure sensor and commands from a user, and a display unit displaying the data from the injection pressure sensor.

Also in accordance with the present invention, there is provided a method of extracting marrow from a vertebra, comprising injecting a thick liquid in the vertebra through a single pedicle, displacing the marrow with the thick liquid, and extracting the marrow through said single pedicle simultaneously with the thick liquid injection by creating a pressure gradient between the injecting and extracting.

Also in accordance with the present invention, there is provided a method of rinsing marrow within a vertebra, comprising inserting a cannula in the vertebra, injecting a liquid in the vertebra through a first conduit of the cannula, aspirating the marrow and bone fluid through a second conduit of the cannula and creating a pressure gradient between the first conduit and the second conduit.

Also in accordance with the present invention, there is provided, in combination, a cannula and a syringe body, the cannula defining an injection conduit having a constant diameter throughout a length thereof, and the syringe body includes a tapered distal end defining an outlet connected to the injection conduit of the cannula, the tapered distal end providing a progressive and constant diameter reduction between a remainder of the syringe body and the injection conduit.

Also in accordance with the present invention, there is provided a viscosity sensing unit for a bone cement delivery device, the unit comprising at least one sensor for measuring a physical parameter of the bone cement directly within the bone cement delivery device, the at least one parameter being indicative of a viscosity of the bone cement, and a display unit receiving data from the sensor and displaying at least one of the physical parameter and the viscosity of the bone cement.

BRIEF DESCRIPTION OF THE DRAWINGS

Reference will now be made to the accompanying drawings, showing by way of illustration particular embodiments of the present invention and in which:

FIG. 4 is a side cross-sectional view of a screw delivery mechanism of the cannula of FIG. 3 according to a particular embodiment of the present invention;

FIG. 5A is a side cross-sectional view of a cannula according to an alternate embodiment of the present invention;

FIG. 6 is tridimensional view of a proximal end of a cannula, which may be for example the cannula of any one of FIGS. 2 to 5C, including a membrane according to a particular embodiment of the present invention;

FIG. 7 is a schematic tridimensional view of a proximal end of a cannula, which may be for example the cannula of any one of FIGS. 2 to 5C, including an intravertebral pressure sensor according to a particular embodiment of the present invention;

FIG. 11 is a schematic side view of a syringe and cannula assembly according to a particular embodiment of the invention;

FIG. 12 is a schematic side view of a syringe including injection pressure sensors according to a particular embodiment of the present invention;

FIGS. 13A-13C are schematic front views of syringes including different ultrasound viscosity sensors according to alternate embodiments of the present invention;

FIG. 14 is a tridimensional schematic view of a syringe including a dielectric viscosity sensor according to an alternate embodiment of the present invention;

FIGS. 15A-15B are front and bottom schematic views of a syringe plunger including a dielectric or electro-resistive viscosity sensor according to an alternate embodiment of the present invention;

FIG. 16 is a graphical representation of an example of the Root Mean Square of an ultrasound pulse of the ultrasound sensors of FIGS. 13A-13C;

DETAILED DESCRIPTION OF PARTICULAR EMBODIMENTS

Figure 1:
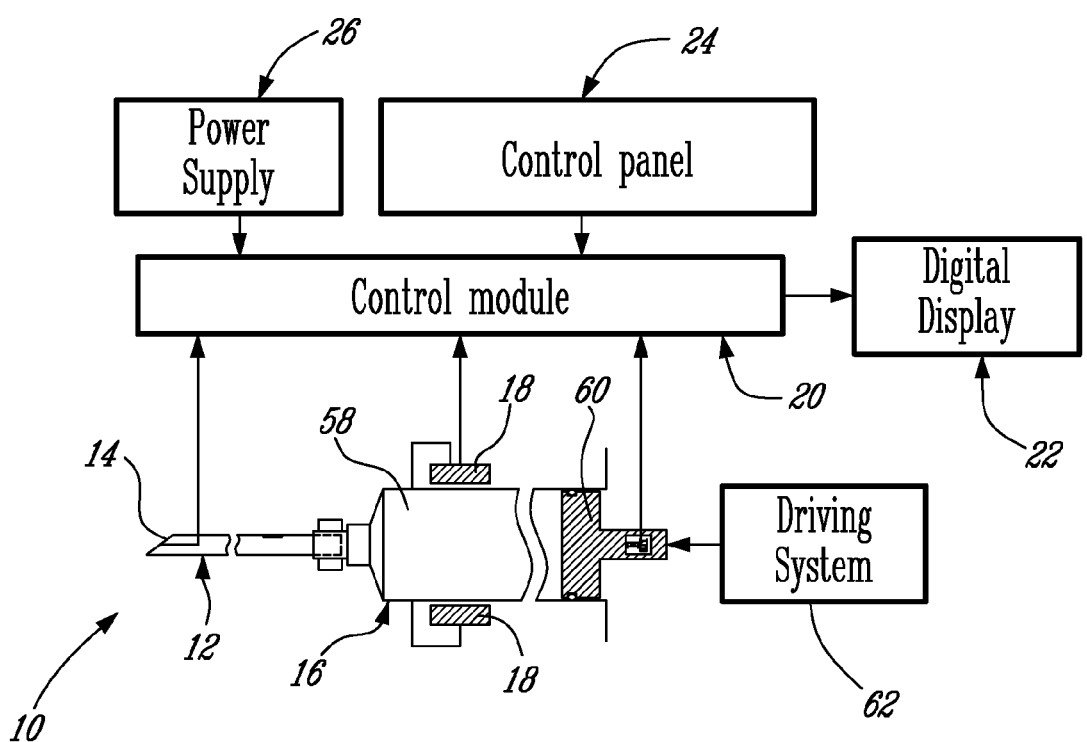
FIG. 1 is schematic representation of a cement delivery system according to a particular embodiment of the present invention.

Referring generally to FIG. 1, a cement delivery system according to a particular embodiment of the present invention is generally and schematically shown at 10. The system 10 generally comprises a cannula 12 which may include pressure sensors 14 to measure the intravertebral pressure, an assisted cement delivery device 16 delivering cement through the cannula 12 and including miniature viscosity sensors 18 to monitor a viscosity of the cement, a controller or control module 20, such as for example provided in an electronic circuit board including a microprocessor, for controlling or operating the cement delivery device 16, a digital display unit 22 for displaying sensor data during the procedure, a control or regulation panel 24 for receiving instructions from a user, and a power supply 26 providing power to the system 10.

The different elements of the cement delivery system 10 are separately described in more detail in the following.

Cannulae 12

The cannula 12 in FIG. 1 can be a standard cannula or, alternately, one of the cannulae 12a,b,c shown in FIGS. 2 to 7. The cannulae 12a,b,c described below allow for monitoring of the intravertebral pressures and/or aspiration of the vertebral body to drain the bone fluid (e.g. marrow, blood) that is displaced during the cement injection, such as to reduce cement leakage and reduce the risk of emboli. The cannulae 12a,b,c are preferably made of an appropriate type of metal or other rigid material, similarly to known single conduit cannula typically used in bone cement injection procedures.

In the case of vertebroplasty, the total pressure required for cement injection $\Delta p_{inj}$ can be separated into the extravertebral cement delivery pressure $\Delta p_{extra}$ required to force the cement through a cannula, the intravertebral cement infiltration pressure $\Delta p_{inf}$ required to force the cement to penetrate the vertebral cavity, and the intravertebral bone marrow pressure $\Delta p_{mar}$ within the vertebral body due to the hydraulic resistance of the vertebra, i.e. $\Delta p_{inj} = \Delta p_{extra} + \Delta p_{inf} + \Delta p_{mar}$. The extravertebral delivery pressure $\Delta p_{extra}$ is generally the largest (e.g. up to 500 psi for mechanical injectors), while the infiltration pressure $\Delta p_{inf}$ and the bone marrow pressure $\Delta p_{mar}$ are generally much lower (e.g. 50 psi and 5 psi, respectively).

Monitoring of the internal bone pressure, or, in the case of vertebroplasty, of the intravertebral pressure (i.e. the infiltration pressure $\Delta p_{inf}$ and the bone marrow pressure $\Delta p_{mar}$) ensures that there is no excess pressure in the bone (vertebral) cavity when delivering cement, as an elevated pressure may cause the cement to spread suddenly in uncontrolled fashion or cause lung emboli. The monitoring of the internal or intravertebral pressure can also be used as a predictor of leakage, since a sudden pressure drop may indicate the existence of a path of least resistance leading to cement leakage. The monitoring of the internal or intervertebral pressure thus allow for prevention of these complications.

Knowledge of the internal or intravertebral pressures also allows for the determination of the pressure within the cannula (e.g. extravertebral), which creates a diagnostic tool for the case in which the physician is not in a position to deliver cement, for example indicating that the cannula is plugged or that the cement is not going into the bone (vertebral body).

Figure 2:
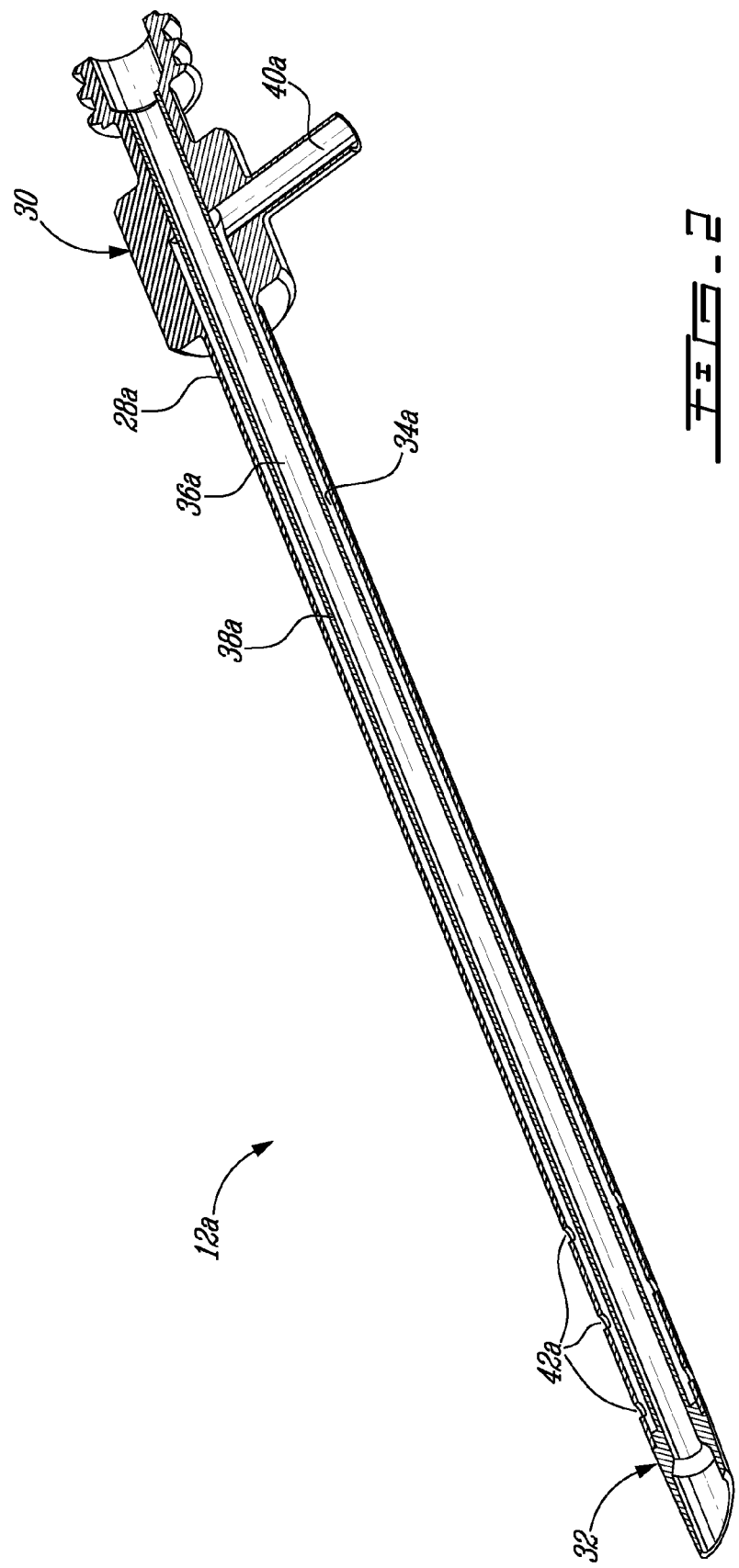
FIG. 2 is a tridimensional cross-sectional view of a cannula according to a particular embodiment of the present invention.

Referring to FIG. 2, the cannula 12a includes an outer tubular wall 28a defining a proximal end 30 and a distal end 32. Concentric peripheral and central conduits 34a, 36a are separated by a thin tubular internal wall 38a extending in the cannula 12a spaced apart from the outer tubular wall 28a. The cannula 12a includes a side outlet 40a defined at the proximal end 30 and a series of fenestrations 42a defined at the distal end 32, both of which being in communication with the peripheral conduit 34a. The central conduit 36a is used to deliver the cement, while the peripheral conduit 34a is used to aspirate the vertebra to aspirate bone fluid (e.g. marrow, blood) during cement injection, or to measure the intravertebral cement infiltration or bone marrow pressures $\Delta p_{inf}$ or $\Delta p_{mar}$ through a pressure sensor 14 (see FIG. 1).

In the case where the peripheral conduit 34a is used to aspirate the vertebra, the fenestrations 42a represent a vent or a sink for the displaced bone fluid when the cement enters the vertebral cavities. In a particular embodiment, the aspiration is done manually using a standard syringe attached to the side outlet 40a to create a vacuum while the physician delivers the cement and to remove the bone fluid. In a more preferred embodiment, the aspiration is done in an automated manner and more specifically, in a volume controlled manner. The automated aspiration allows for cement to be injected at a given flow rate and for bone fluid to be aspirated at a slightly higher flow rate, such that the cement follows the displaced bone fluid and takes its place. One practical way of producing the vacuum for the automated aspiration is to use a vacuum pump connected to the side outlet 40a and applying for example a low-level vacuum in the range of 10 to 100 KPa. The vacuum pump is preferably regulated by a vacuum regulator (e.g. mechanical or electronic), which is regulated by the control module 20 as will be described in a following section.

In addition to removing bone fluid, the aspiration or vacuum creates a pressure gradient between the central conduit 36a and the peripheral conduit 34a, which creates a hydraulic force guiding the displacement of the bone fluid and the flow of the cement. This pressure gradient can be used to guide the cement flow to facilitate controlled and predictable filling with enhanced mechanical efficacy and reduced cement emboli.

In a particular embodiment where the peripheral conduit 34a is used to measure the intravertebral cement infiltration or bone marrow pressures $\Delta p_{inf}$ or $\Delta p_{mar}$, the pressure sensor 14 (see FIG. 1) is provided at the proximal end of the peripheral conduit 34a, and either air or liquid is used as a media to transfer the pressure wave generated in the vertebra when delivering cement from the distal end 32 of the cannula to the pressure sensor 14.

The cannula 12a may feature different fenestration patterns at its distal end 32 that that shown in order to meet different functions.

Figure 3:
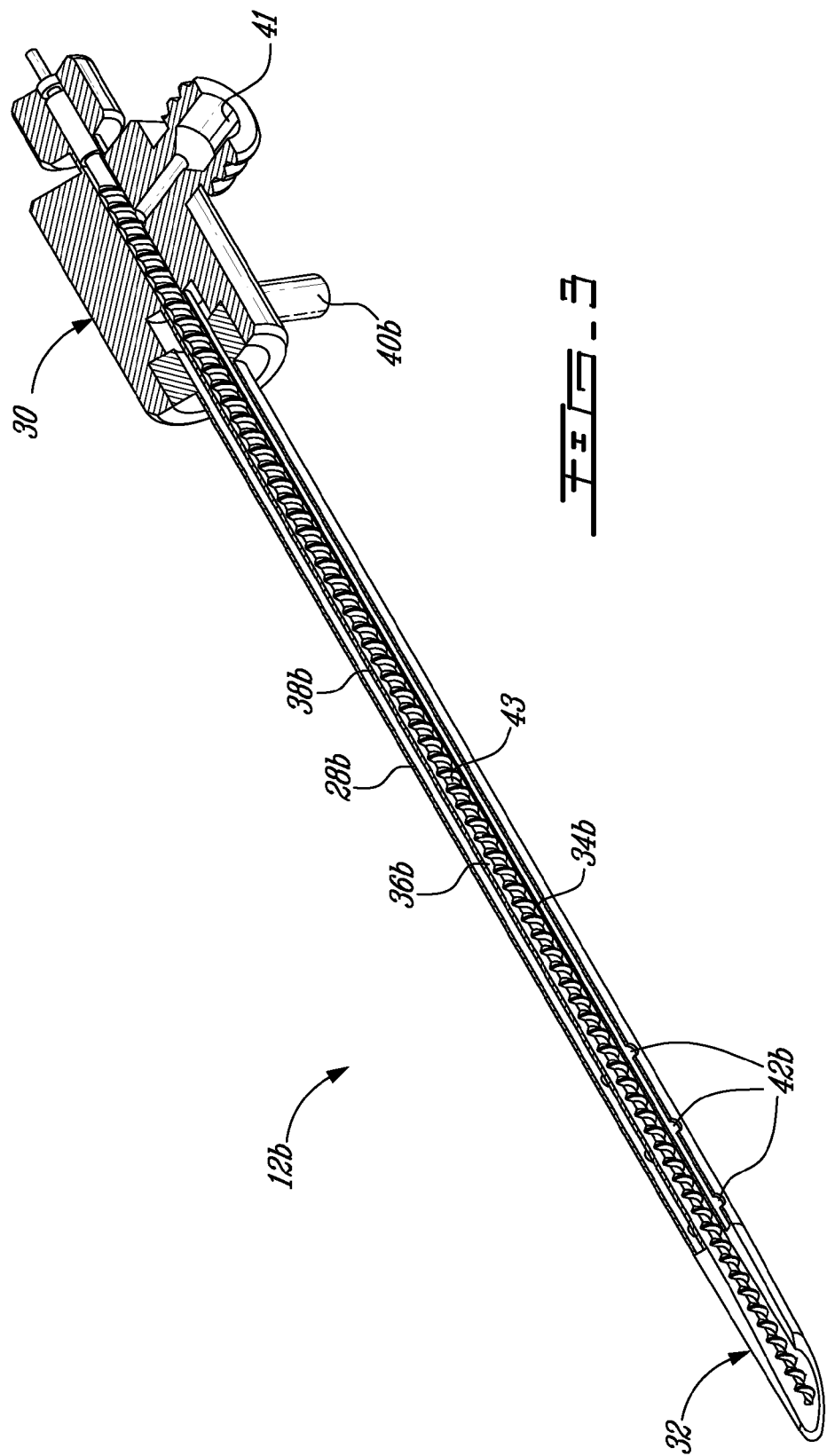
FIG. 3 is a tridimensional cross-sectional view of a cannula according to an alternate embodiment of the present invention.

The cannula 12b shown in FIG. 3 is similar to the cannula 12a, and includes an outer tubular wall 28b, concentric peripheral and central conduits 34b, 36b separated by a thin tubular internal wall 38b spaced apart from the outer tubular wall 28b, as well as a side outlet 40b at the proximal end 30 and a series of fenestrations 42b at the distal end 32 which are both in communication with the peripheral conduit 34b. Like the cannula 12a, the central conduit 36b of the cannula 12b is used to deliver the cement while the peripheral conduit 34b is used to aspirate and drain the bone fluid as described above, or to measure the intravertebral cement infiltration or bone marrow pressures $\Delta p_{inf}$ or $\Delta p_{mar}$ through a pressure sensor 14 (see FIG. 1).

However, the cannula 12b also includes a side inlet 41 defined at the proximal end 30 in communication with the central conduit 36b, through which the cement enters the cannula 12b. The cannula 12b additionally includes a screw delivery mechanism 43 extending within the central conduit 36b along its length. In a particular embodiment, the screw delivery mechanism 43 is either a helical or spiral transport screw. The rotating screw delivery mechanism 43 facilitates the transport of the cement through the central conduit 36b in a precise manner.

The cannula 12b is thus especially useful for injecting cements that are difficult to inject because of phase separation, such as for example calcium phosphate (CaP), with the screw delivery mechanism 43 increasing the mixing of the cement to reduce the risk of phase separation. The screw delivery mechanism 43 also significant decreases the pressure required for cement delivery since the cement delivery by the screw delivery mechanism 43 requires little pressure when compared with simply pushing the cement though the elongated geometry of the cannula, and as such can also be used to transport thick PMMA cement. The use of thick cement reduces the risk of leakage, while the use of the screw delivery mechanism 43 facilitates the cement delivery without the need for excessive forces.

Although the rotation of the screw delivery mechanism 43 can be applied manually, in a particular embodiment the rotation is applied by a micro motor (not shown). As such, the pressure drop in the cannula 12b is overcome by the power of the micro-motor and the physician does not contribute to overcoming this pressure. The rotation speed of the screw delivery mechanism 43 is regulated, for example by the control module 20 as will be further described below, to adjust for the desired delivery flow rate. As such, the physician can shift focus on the patient and on the surgery instead on being focused on delivering sufficient cement in the intervention. In a particular embodiment, where the central conduit 36b and screw 43 are designed for cement delivery at a speed 3 ml/minute, the micro-motor rotating the screw delivery mechanism 43 provides a power of approximately 52 mW.

In a particular embodiment, the screw delivery mechanism 43 is a typical delivery screw. However, in an alternate embodiment shown in FIG. 4, the screw delivery mechanism 43 is cannulated, i.e. an inner conduit 37 is defined within the screw delivery mechanism 43 along its length. This inner conduit 37 is preferably instrumented to measure the intravertebral cement infiltration pressure $\Delta p_{inf}$, with either air or liquid being used for the transfer of the infiltration pressure from the distal end of the screw to the proximal end of the screw, where a pressure sensor 14 (see FIG. 1) is mounted. The screw 43 may additionally feature radial fenestrations or vents that connect directly to its inner conduit 37. The peripheral conduit 34b is used to measure the intravertebral bone marrow pressure $\Delta p_{mar}$ or to aspirate the bone fluid as the bone cement is delivered through the central conduit 36b.

Figure 5B:
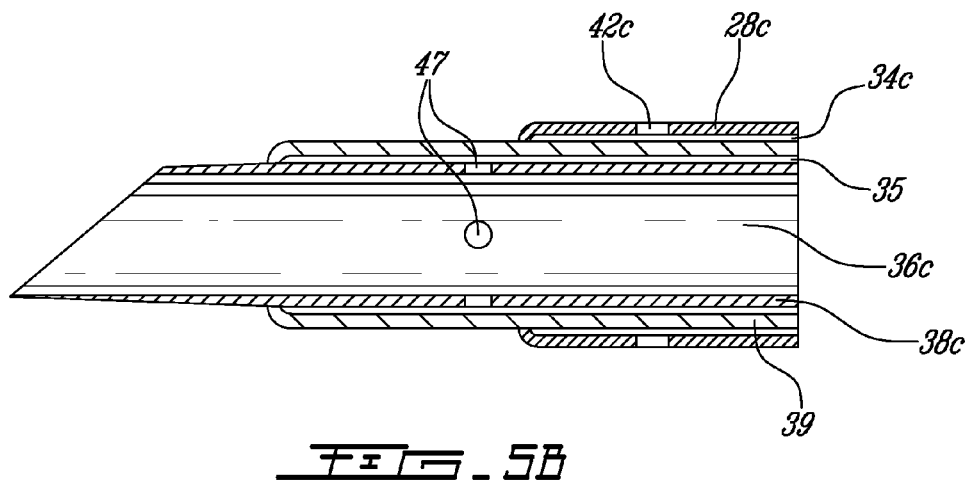
FIG. 5B is an enlarged, side cross-sectional view of a portion of the cannula of FIG. 5A.
Figure 5C:
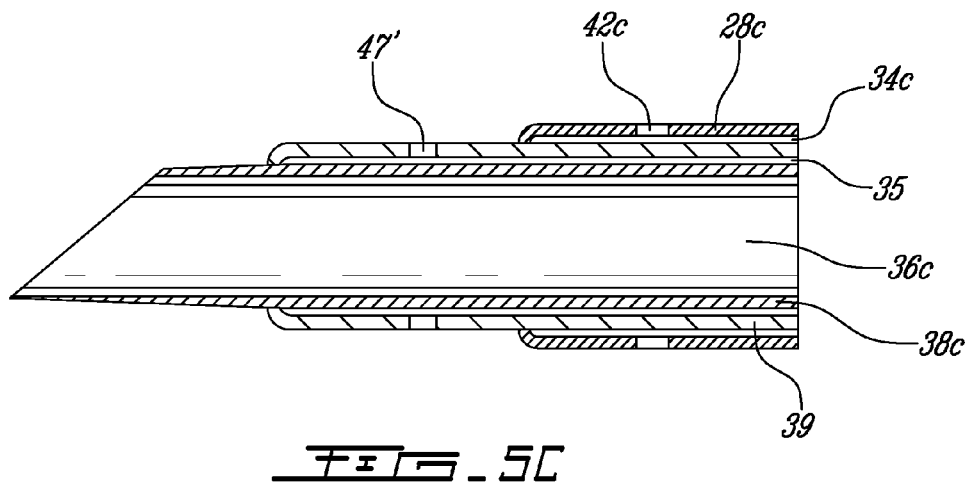
FIG. 5C is an enlarged, side cross-sectional view of a portion of the cannula of FIG. 5A according to an alternate embodiment of the present invention.

The cannula 12c shown in FIGS. 5A-5C includes concentric tubular inner, middle and outer walls 38c, 39, 28c, thus defining central, middle and peripheral concentric conduits 36c, 35, 34c. A side outlet 40c (see FIG. 5A) defined at the proximal end 30 and a series of fenestrations 42c (see FIGS. 5B-5C) at the distal end 32 are both in communication with the peripheral conduit 34c. A second side outlet 45 defined at the proximal end is in communication with the middle conduit 35. The central conduit 36c is used to deliver bone cement.

Referring particularly to FIG. 5B, in one embodiment, fenestrations 47 are defined through the inner wall 38c, and the middle conduit 35 is used to measure the intravertebral cement infiltration pressure $\Delta p_{inf}$ while the peripheral conduit 34c is used to aspirate the bone fluid or to measure the intravertebral bone marrow pressure $\Delta p_{mar}$. As described above, in a particular embodiment a pressure sensor 14 (see FIG. 1) is mounted to the proximal end of the middle conduit 35 and either air or liquid is used as a media to transfer the pressure wave generated in the vertebra when delivering cement from the distal end 32 of the cannula to the pressure sensor 14.

In another embodiment shown in FIG. 5C, the fenestrations 47' are alternately defined through the middle wall 39, and one of the middle and peripheral conduits 35, 34c is used to measure the intravertebral bone marrow pressure $\Delta p_{mar}$ while the other is used to aspirate the bone fluid.

Alternately, the screw delivery mechanism 43 of the cannula 12b, with or without its inner conduit 37, can be integrated in a single conduit cannula or in a cannula having three conduits such as 12c.

The cannulae 12a,b,c thus allow for the bone fluid to be aspirated and the cement to be injected simultaneously and using a same operative site, without the need to use separate cannulae, which reduces the risks of complications.

The cannulae 12a,b,c can also advantageously be used to rinse the bone marrow and create a path favoring cement flow. Prior methods of rinsing the bone marrow usually necessitate the use of two separate surgical sites. With the cannulae 12a,b,c, pulsating or non pulsating fluid is injected through one of the conduits, creating a pressure gradient between the conduits and allowing for the rinsing process to be performed using a single cannula and thus a single surgical site. The rinsing process is done manually or automatically with the help of an automated system, applying a level of pressure similar to the one applied for bone fluid extraction. In an alternate embodiment, the rinsing process is performed through a smaller diameter tubing extending within the cannula (either 12a,b,c or single conduit cannula) extending deeper within the vertebra.

FIG. 6 shows a membrane 44 which is optionally attached at the distal end 32 of the central conduit 36a,b,c of any one of the cannulae 12a,b,c described above or, alternately, at the distal end of a single conduit cannula. The membrane 44 is preferably elastic and retractable, and has a permeability (illustrated by holes 46) that is roughly ten percent (10%) of the permeability of osteoporotic cancellous bone. The size and elasticity of the membrane 44 is preferably such as to define an expanded diameter of no more than 5 millimeters to ensure the least damage to the surrounding bone. The membrane 44 can be made of fabric tissue or preferably super elastic metals.

When the cement is delivered, it expands the membrane 44 and generates a state of uniform hydrostatic pressure inside the membrane 44. Specifically, the rate of cement flow exterior to the membrane 44 is controlled by the pressure gradient between the membrane 44 and the surrounding bone. The intravertebral pressure in the surrounding bone is insignificant, thereby imposing a constant uniform pressure gradient on the surface of the membrane 44. This uniform gradient leads to uniform and controlled flow of the cement through the membrane 44 and in the environment. The membrane 44, due to the low permeability, is thus the guiding tool for the intravertebral flow. Thus, the membrane 44 ensures controlled slow and uniform expansion of the cement, and prevents preferential pressure gradients caused by local bone morphology and thereby, ensuring seepage flow and likely reducing leakage risk.

In the case where the internal bone pressure (e.g. intervertebral pressure) is not measured through a separate conduit of the cannula, the cannula preferably includes a pressure sensor 14 as shown in FIG. 7, such as a miniature MEM sensor, which is placed directly at its distal end 32 while ensuring that the flow is not obstructed. This provides direct readings of the internal or intravertebral pressure during the cement delivery process.

As mentioned above, any one of the cannulae 12*a,b,c* can take the place of the cannula 12 in the cement delivery system shown in FIG. 1. The cannulae 12*a,b,c* present the advantage of allowing for multiple operations (cement delivery and pressure measurements and/or bone marrow extraction and/or bone marrow rinsing) using a single site.

Although the cannulae 12*a,b,c* have been described mostly with relation to vertebroplasty, the cannulae 12*a,b,c* can alternately be used in other cement augmentation procedures where cement is injected into other anatomical locations (such as osteoporotic femur and distal radius) and where similar issues of high pressure exist. Additionally, the cannulae 12*a,b,c* can also be used in any appropriate type of percutaneous injection of viscous biomaterials into the human body (e.g., drug delivery using carriers, biometrices for tissue engineering).

In addition, the cannulae 12*a,b,c* can advantageously be used for bone marrow extraction for graft, blood disorders, stem cell transplantation or orthopedic procedures. Known methods of performing bone marrow extraction include directly using a syringe to remove the bone marrow, generally extracting mostly blood and a small quantity of marrow. With the cannulae 12*a,b,c*, a thick liquid is delivered through one of the conduits, invading the bone cavity saturated by bone marrow and as such displacing the bone marrow, which is then guided through suction into another conduit of the cannula, thus increasing the efficiency of the bone marrow extraction procedure.

Cement Delivery Device 16

It has been shown that when a fairly liquid cement is injected into a vertebra, the cement finds and flows through a path of least resistance, however when the cement is injected at a viscosity or degree of curing that is high enough, it expands uniformly as if the path of leakage did not exist. Accordingly, by controlling the time of injection and thereby the cement viscosity, the incidence of leakage can be reduced considerably. The challenge is that cement generally ceases to be manually injectable with a standard syringe and cannula at about the minimal viscosity avoiding flowing through the path of least resistance.

Referring back to FIG. 1, the cement delivery device 16 generally includes a syringe body 58 and a syringe plunger 60 which is displaced within the body 58 by any adequate driving system 62, such as for example an electric motor, a pneumatic system or an hydraulic system. The driving system 62 is controlled or regulated by the control module 20, as will be described in a following section, such that the displacement of the plunger 60 is controlled, preferably advancing in a continuous manner (i.e. in a consecutive series of steps of equal duration and equally spaced apart, or with an uninterrupted motion at a constant speed) in the syringe body 58, such as to precisely deliver a given volume of cement, thus reducing undesired excess cement which increases leakage risks. In a particular embodiment, the driving system 62 allows for the delivery of a desired volume of cement with a precision of 50 micro liters. The driving system 62 generates an axial force on the plunger 60 which generates an injection pressure substantially greater than human physical limits and sufficient to deliver the cement, thus overcoming the limitation of excessive pressure and increasing the chances of being able to complete the procedure adequately. In a particular embodiment, the axial force generated by the driving system 62 is approximately 2 KN. The increased injection pressure ensures the delivery of thicker cement, which substantially reduces the risks of cement leakage.

The driving system 62 delivers the cement continuously and slowly, for example at 3 ml/minute, and in a particular embodiment, at most 10 ml/minute, resulting in a steady flow which enhances cement filling uniformity and reduces leakage risks by reducing undesired transient peaks in pressure.

The driving system 62 allows for a displacement controlled delivery which leads to stable flow conditions, thereby reducing the risk of sudden uncontrolled flow in the case of leakage.

Figure 8:
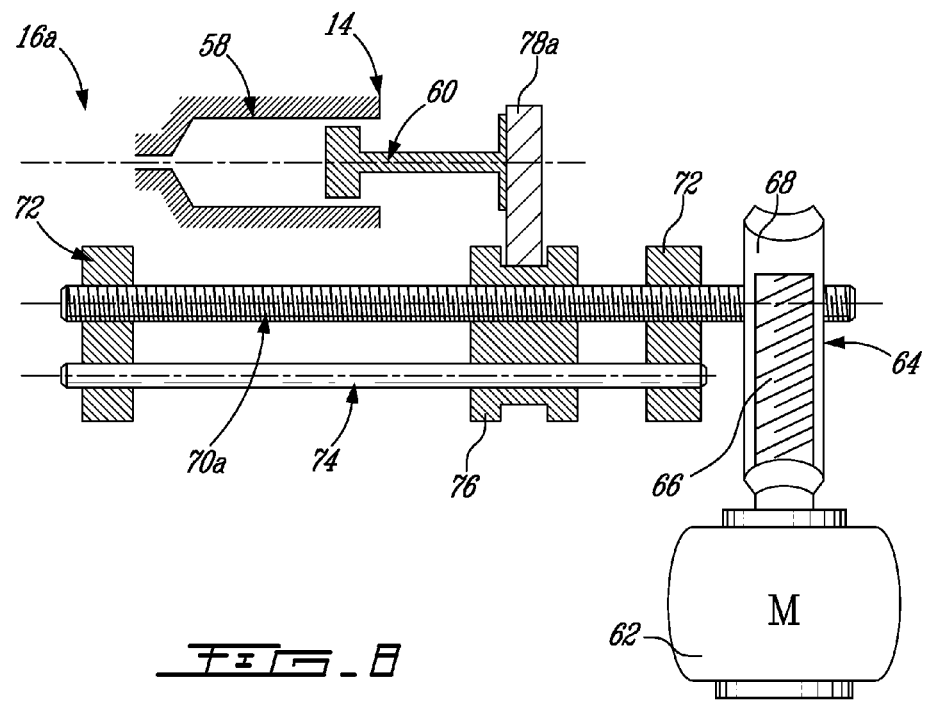
FIG. 8 is a schematic side view of a cement delivery device according to a particular embodiment of the present invention.

Referring to FIG. 8, a particular embodiment 16*a* of the cement delivery device 16 is shown. The cement delivery device 16*a* includes a worm gear speed reduction mechanism 64 connected to the driving system 62, depicted here as an electric motor. The motor 62 powers the endless screw component 66 of the worm gear mechanism 64, which turns the wheel component 68 that rotates a threaded rod 70*a*. The threaded rod 70*a* is rotationally supported between two supports 72, which also support a guidance rod 74 extending therebetween. A nut 76 is slidably retained by the guidance rod 74 and threadingly engaged to the threaded rod 70*a*. The rotation of the threaded rod 70*a* causes a lateral motion of the nut 76 and of a pushrod 78*a* connected thereto, the pushrod 78*a* activating the movement of the syringe plunger 60 within the body 58 of the syringe 114 to inject the cement. The guidance rod 74 ensures steady movement of the pushrod 78*a* for accurate cement delivery.

A number of alternate embodiments are possible. For example, in one alternate embodiment, the nut 76 is omitted, and the rotation of the threaded rod 70*a* directly applies a lateral force to the pushrod 78*a* which is threadingly engaged therewith and slidably received on the guidance rod 74. In another alternate embodiment, the pushrod 78*a* is omitted, and the nut 76 directly activates the movement of the plunger 60. In another alternate embodiment, the guidance rod 74 and pushrod 78*a* extend on opposed sides of the syringe body 58 for improved stability. In another alternate embodiment, the supports 72 can directly support and guide the threaded rod 70*a*, pushrod 78*a* and/or nut 76, and as such the guidance rod 74 can be omitted. In another alternate embodiment, the pushrod 78*a* or the nut 76 acts directly as the syringe plunger 60, thus reducing the number of necessary elements. Other modifications are also possible.

Figure 9:
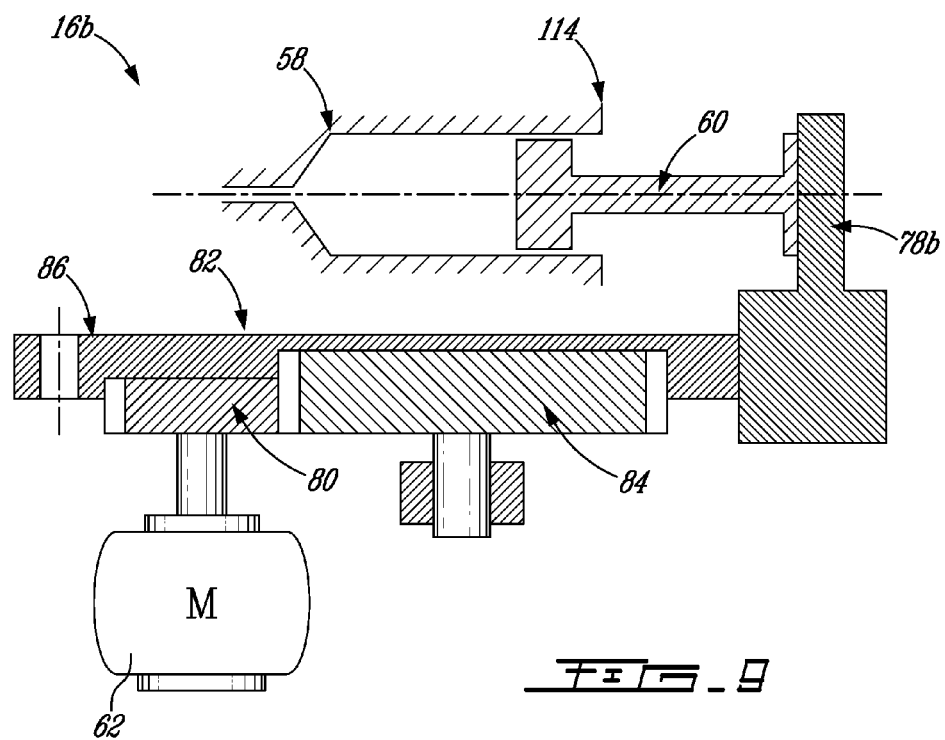
FIG. 9 is a schematic side view of a cement delivery device according to an alternate embodiment of the present invention.

Referring to FIG. 9, another particular embodiment 16*b* of the cement delivery device 16 is shown. The cement delivery device 16*b* includes a spur gear and toothed rack speed reduction mechanism 82 connected to the driving system 62, shown here as an electric motor, through a pinion 80. The motor 62 rotates the pinion 80, which rotates the spur gear 84 of the mechanism 82, which in turn forces the movement of the toothed rack 86. The rack 86 is fixed to the pushrod 78*b*, so the movement of the rack 86 applies a lateral force to the pushrod 78*b* which activates the movement of the syringe plunger 60 inside the body 58 of the syringe 114 and forces the injection of the cement.

Figure 10:
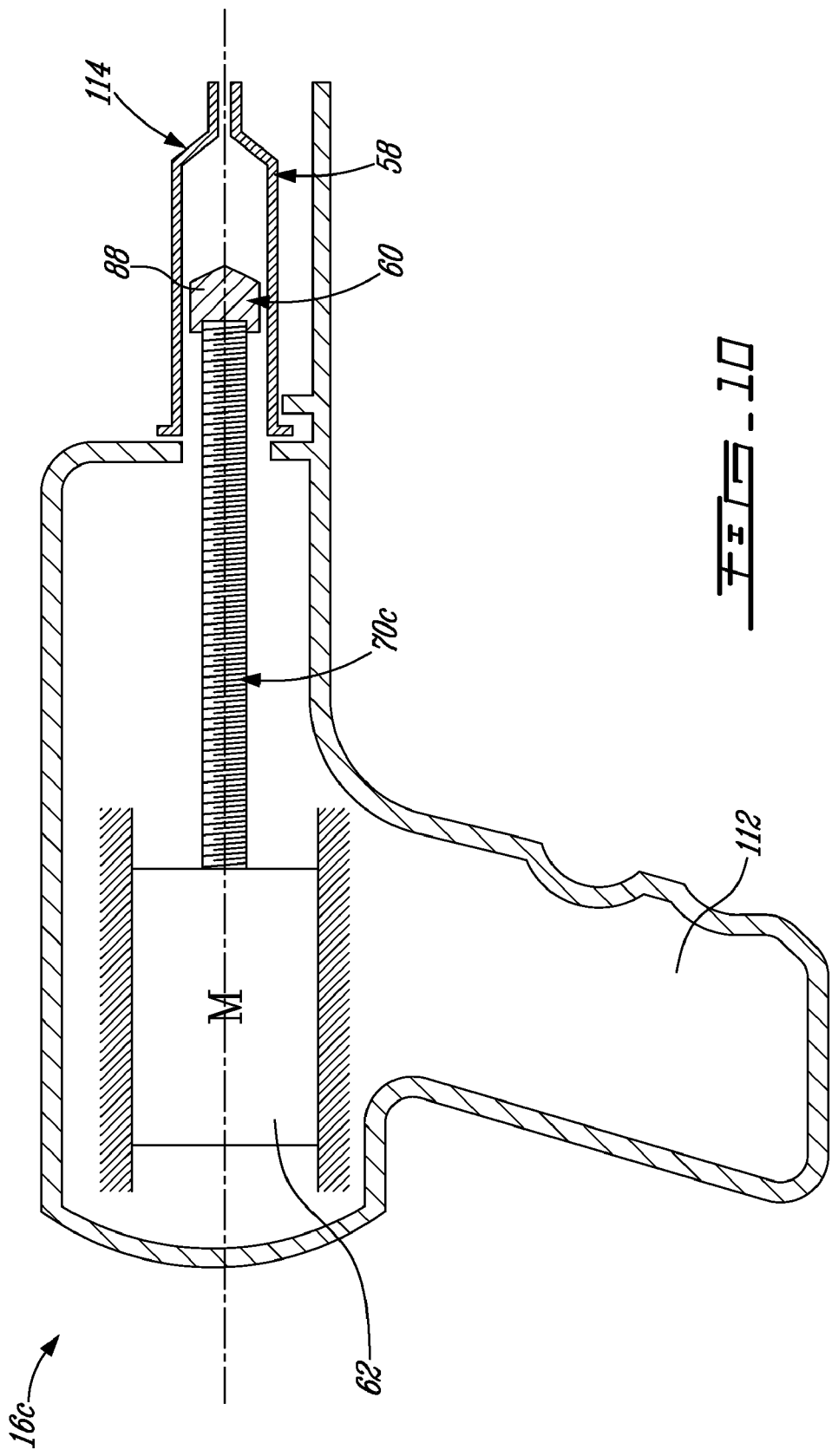
FIG. 10 is a schematic side view of a cement delivery device according to an alternate embodiment of the present invention.

Referring to FIG. 10, another particular embodiment 16*c* of the cement delivery device 16 is shown. The cement delivery device 16*c* is simple and the driving system 62, whether electrical, pneumatic, hydraulic or other, is a linear motor, directly rotating and translating a threaded rod 70*c*. The threaded rod 70c is attached to an interchangeable head 88 that acts as the plunger 60 within the body 58 of the syringe 114. The lateral movement of the head 88 forces the injection of the cement.

Accordingly, any one of the devices 16a,b,c can take the place of the cement delivery device 16 in the cement delivery system 10 shown in FIG. 1.

Any one of the devices 16a,b,c can also be used in any appropriate orthopedic application where medical cement is injected.

Referring to FIG. 11, as suddenly contracting geometry from the cement delivery device 16 to the cannula 12 in conventional procedures can causes a substantial increase in injection pressure, in a particular embodiment the geometrical transition from the device 16 to the cannula 12, 12a,b,c is adapted, thereby minimizing unnecessary pressure loss. The diameter of the central conduit 36a,b,c of the cannula is constant, even in its proximal end 30, where the outer tubular wall 28a,b,c defines a connection element 87 such as for example a male Luer lock adapter. The syringe body 58 is tapered, for example defining a conical shape extending at an angle α (which in a particular embodiment is approximately 45°) from a remainder of the syringe body 58, up to a complementary connection element 89, such as for example a complementary female Luer lock adapter, surrounding the connection element 87 of the cannula 12, 12a,b,c. This provides a smooth transition between the diameter of the major part of the syringe body 58 and the constant diameter of the central conduit 36a,b,c, thus lowering the overall injection pressure, and as such facilitating the delivery of thicker cements. Such a connection can alternately be used in other types of syringes and delivery systems for cements or other thick medium, including manual delivery systems.

Referring to FIG. 12, in a particular embodiment the cement delivery device 16 (16a,b,c, or other) is instrumented to measure the injection pressure. The device 16 comprises injection pressure sensors 90 including a strain gauge bridge 92 embedded directly in the syringe plunger 60, such as to measure the overall injection pressure during the cement delivery process. In an alternate embodiment, the injection pressure sensors 90 include a force or loading cell embedded between the plunger and the displacing mechanism of the plunger. An example for such a load cell is a cylindrical load cell with two threads protruding from both sides.

The injection pressure can be calculated once the injection force and the cross-sectional area of the syringe are known. The injection pressure sensors 90, whether in the form of force sensors or in any other adequate form, can alternately be included in any other appropriate location of the cement delivery device 16, 16a,b,c, such as for example within the driving system 62.

With the knowledge of the injection pressure and of the internal bone pressure (e.g. intravertebral), the pressure drop in the cannula 12 can be determined, and as such, based on the known injection speed and cannula dimensions, the viscosity of the cement can be determined through Hagen-Poiseuille's law.

Viscosity Sensor 18

As shown in FIG. 1, the cement delivery system 10 further includes viscosity sensors 18 providing continuous viscosity or curing readings of the polymerizing cement in the cement delivery device 16, without introducing any significant changes to the technique of vertebroplasty.

The role of cement viscosity or the degree of polymerization plays a significant part in the safety of vertebroplasty. More specifically, cement having a higher viscosity enhances the uniformity of the cement filling, thereby reducing the risk of cement leakage. Specifically, the viscosity sensors 18 monitor changing physical properties triggered by the cement polymerization. In particular embodiments, the sensors monitor acoustic properties of the cement, while in alternate embodiments the sensors monitor electrical properties of the cement. Alternately, other properties of the cement can be monitored, for example using piezo-electric sensors, a conductive grid, photonic sensors, reflective sensors, spectroscopic sensors, etc. The viscosity sensors 18 can be used in vertebroplasty but also in cement guns or delivery systems used in arthroplasty, or in any medical intervention where bone cements are used and where physicians require cement viscosity readings.

In particular embodiments shown in FIGS. 13A-13C, the miniature viscosity sensors 18a,b,c include an ultrasound emitter 94a,b,c and an ultrasound receiver 96a,b,c positioned around the syringe body 58. The emitter 94a,b,c sends out an ultrasound signal that goes through the cement and reaches the receiver 96a,b,c. The sensors 18a,b,c measure the pulse attenuation, time delay, traveling speed, and the intensity of the ultrasound signal. These quantities change as the cement polymerizes in the syringe body 58. When these readings are known, the cement properties are determined accurately. The sensors 18a,b,c are non-invasive and non-intrusive, forming an integral and reusable part of the cement delivery system 10. The ultrasound signal can be longitudinal or transversal.

In the embodiment shown in FIG. 13A, both the emitter 94a and receiver 96a of the sensor 18a are integrated into one unit. In the embodiment shown in FIG. 13B, the emitter 94b and receiver 96b of the sensor 18b are two isolated entities or components that are located at the opposite sides of the syringe body 58. In the embodiment shown in FIG. 13C, the receiver 96c and emitter 94c are positioned at two different locations one a same side of the syringe body 58.

The initial pulse and the attenuated pulse are triggered, controlled or regulated and analyzed by the control module 20 (see FIG. 1), as will be described in a following section.

The display unit 22 (see FIG. 1) displays various information obtained from the sensors 18a,b,c, which include for example: the attenuation or dampening of the original signal compared to the received signal, the velocity at which the signal travels through the cement, the delay time which is the time taken by the pulse to travel through the cement, and the Root mean square (RMS) which measures the intensity of the received signal. The delay time and the velocity are interrelated because of the fixed diameter of the syringe.

In alternate embodiments shown in FIGS. 14-15 the miniature viscosity sensors 18d,e include dielectric or electro-resistive sensors. The dielectric sensors measure the capacitive and conductive properties of the polymerizing cement, and the electro-resistive sensors measure the resistive properties of the cement. An advantage of the dielectric and electro-resistive sensors is that they can be integrated in the electronic circuit board including the control module 20.

In the embodiment shown in FIG. 14, the dielectric sensor 18d is reusable and is an integral component of the cement delivery system 10. This sensor 18d comprises two thin metallic plates 98 with a convex geometry, or any other appropriate geometry, adapted to partially surround the syringe body 58 and defining a capacitor or condenser. The two plates 98 are spring loaded through springs 100. Once the standard syringe body 58 is placed between the two plates 98, the springs 100 clamp the syringe body 58 and ensure direct physical contact between the two plates 98 and the syringe body 58 filled with the cement. An alternating current is sent through the two plates 98 and the reading of the capacitive and conductive changes on the digital display provide information on the cement polymerization process.

In a particular embodiment, the syringe body 58 has an elliptical or rectangular cross-section, which increases the uniformity of the electric field and as such the stability of the measurements. The rectangular cross-section, or alternately, a square cross-section (the corners of which can be rounded to facilitate sealing with the plunger) advantageously increases the capacity and also provide the advantage of ensuring that the distance between the plates 98 is constant and known, which further increases the stability of the measurements. Alternately, the syringe body 58 can have a more standard round cross-section.

In an alternate embodiment, the plates are integrated into the standard syringe body 58, thereby leading to an instrumented disposable syringe. Electroless metallic coating can be used to coat the syringe body 58 to form the plates. The functional thickness of the plates is preferably no more than a few microns, mainly because of the capacitive and conductive changes that take place on the atomic level. In a non-invasive version of the sensor, the thin plates are placed on the outer surface of the syringe body 58, in a geometry similar to that of the plates 98 shown in FIG. 14 to define a capacitor or condenser. In an invasive version of the sensor, which can be either a dielectric or an electro-resistive sensor, the plates are positioned on the inner surface of the syringe body 58 (not shown) or on the tip of the plunger 60 to form the sensor 18*e* shown in FIG. 15. In both cases, the plates act as electrodes of the electro-resistive sensor or as a capacitor of the dielectric sensor. Such instrumented syringes can be produced on a large scale at reasonable cost.

For both reusable and disposable sensors, the electrical signals indicating the change in the capacitive and conductive properties or resistive properties of the cement is processed and analyzed by the control module 20, and displayed on the display unit 22 of the system 10 (see FIG. 1), as will be further detailed in a following section.

Any one of the viscosity sensors 18*a,b,c,d,e* can take the place of the viscosity sensor 18 of the cement delivery system 10 shown in FIG. 1.

The viscosity sensors 18*a,b,c,d,e* can define, together with the display unit 22, a viscosity sensing unit which can be used in any medical intervention where bone cements are used and where physicians require cement viscosity readings, and in combination with any other appropriate cement delivery device 16.

Ultrasound Miniature Viscosity Sensor Experiment

The ultrasound viscosity sensors 18*a,b,c* were tested according to the following. An ultrasound pulse was sent to a 10 cc syringe, and the Root Mean Square (RMS), attenuation, and the velocity were measured. We also examined the use of longitudinal versus transverse ultrasound waves in addition to two frequencies of 1 and 5 MHz, although it should be understood that other frequencies can be used. The emitter and receiver were positioned around the syringe using a custom made holder. A pulse generator was used to trigger the initial pulse. The attenuated pulse received was amplified and displayed on the oscilloscope. The data was processed and analyzed using a pc.

Figure 17:
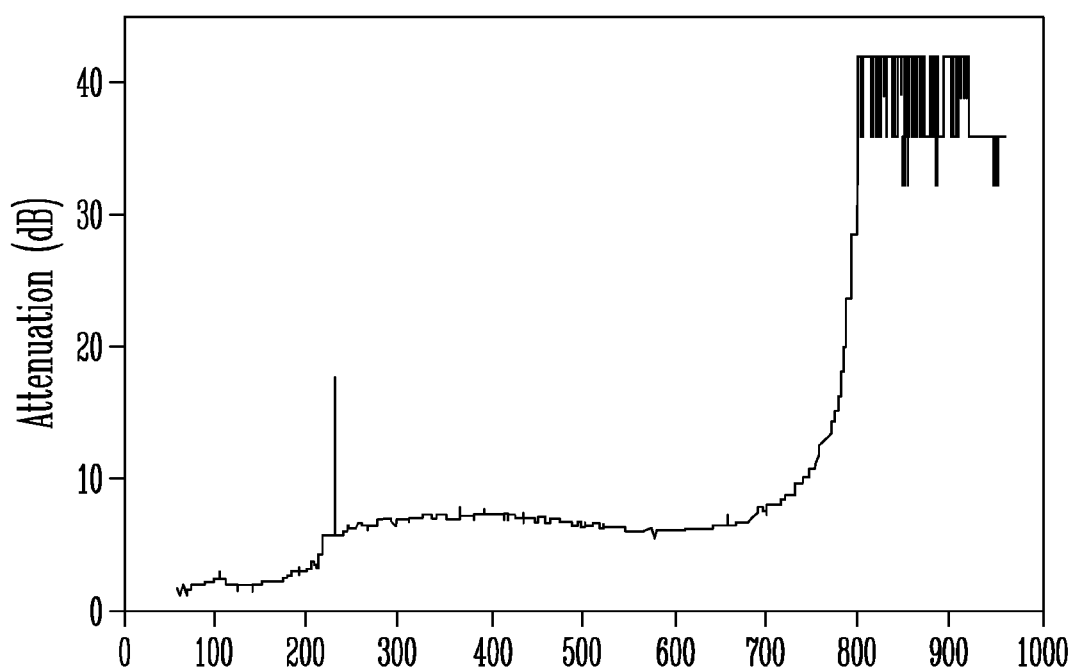
FIG. 17 is a graphical representation of an example of the attenuation of the ultrasound pulse of the ultrasound sensors of FIGS. 13A-13C.

The results of the experiment are shown in FIGS. 16-17. The times indicated in these figures represent the time after cement mixing. Time 0 is the point in time where the two components were mixed. Likewise, time 600 is ten minutes after cement mixing. FIG. 16 shows the evolutions of Root Mean Square (RMS) over the period of polymerization of the cement. The curve shows an initial plateau, followed by a significant drop and a slight increase. The curve also shows interesting features around 600 seconds and 800 seconds after the mixing. FIG. 17 shows the attenuation of the signal over time. Both figures show constant change up to roughly 7 minutes. Within two minutes thereafter, there is a significant increase because of the polymerization. Finally, the signal levels off. These two curves are similar to the viscosity curve or the heat production curve when testing cement in a rheometer or a calorimeter.

Dielectric Miniature Sensor Experiment

The dielectric viscosity sensors 18*d,e* were tested according to the following. In the reusable embodiment, a sensor was custom made to host the syringe filled with cement. In the disposable embodiment, a metallic coating was used to produce the plates on the outer surface of the syringe. Also, some measurements have been taken with an invasive disposable dielectric sensor. For the data acquisition, a RCL meter was used to replace the control module 20 of the system 10 and to measure the capacitive and conductive changes of the cement.

Figure 18:
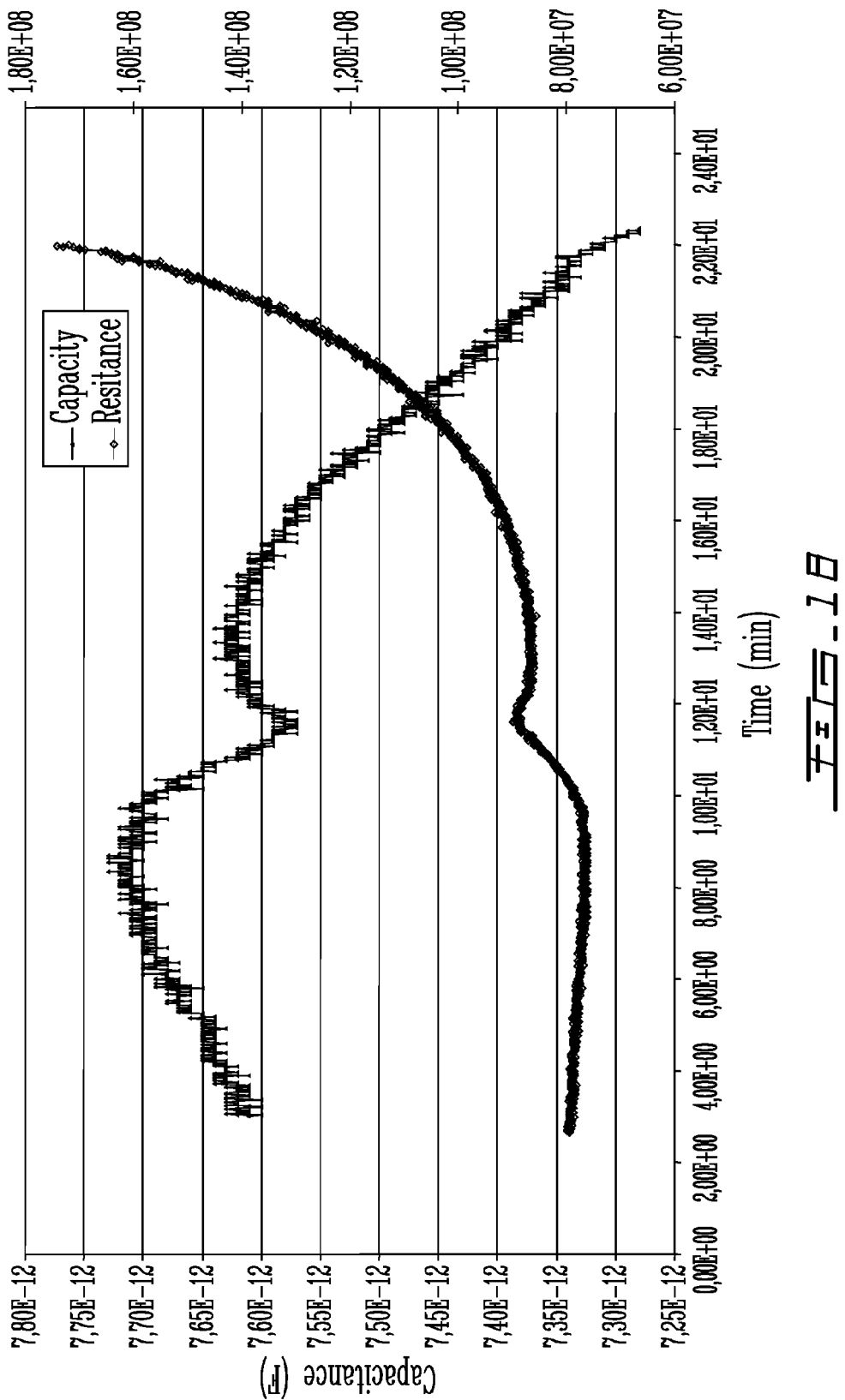
FIG. 18 is a graphical representation of an example of a capacity, resistance, impedance and phase of the dielectric sensors of FIG. 14.

The results are shown in FIG. 18, where the times depicted in the figures indicate the point in time after the cement has been mixed. FIG. 18 shows both the capacitive as well as the conductive changes measured when using the non-contact sensor. It is used as a representation of the results that can be obtained from a dielectric sensor. The figure depicts that significant changes in both capacitive and resistive changes take place as time proceeds and these changes are reproducible and can be used to monitor the advancement of cement polymerization.

Control System 102

Figure 19:
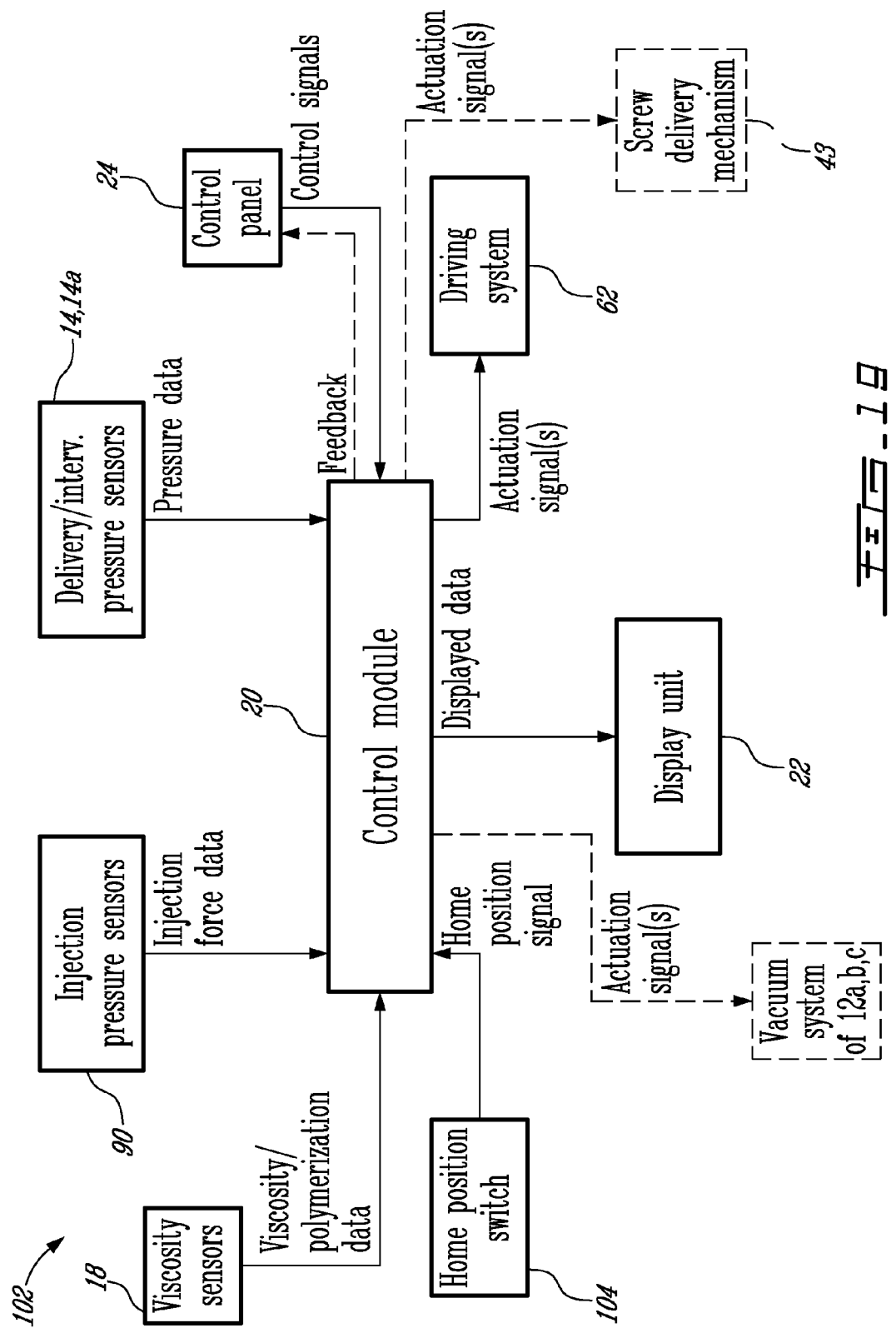
FIG. 19 is a block diagram of a control system according to a particular embodiment of the present invention.

Referring to FIG. 19, in a particular embodiment an integrated cement delivery system such as shown in FIG. 1 includes a control system 102. In a particular embodiment, the control system 102 allows the cement delivery system 10 to enhance the uniformity of the cement filling through the controlled injection of a cement of adequate viscosity in a precise and continuous manner, the regulation of the internal and injection pressures, the immediate depressurization of the vertebra, and the monitoring and feedback provided to the physician.

The control system 102 comprises the control module 20, the intravertebral pressure sensors 14, viscosity/curing sensors 18, injection pressure sensors 90, control panel 24 and a home position switch 104 all sending signals to the control module 20, and the display unit 22 and driving system 62 receiving signals from the control module 20. The home position switch 104 ensures the accurate positioning of the driving system 62. The switch 104 can be, for example, an optical sensor or a mechanical switch, or an external sensor attached to the cannula 12.

The digital display unit 22 is a tool to monitor the cement injection process. The display unit 22 displays data received from the control module 20 such as cement viscosity, total injection pressure, cannula delivery pressure, intravertebral pressure, cement delivery rate or speed, total injected volume, etc. All of these readings are displayed graphically and/or numerically. The display unit 22 can be integrated in the cement delivery device 16 as will be further detailed below. In addition or in the alternative, the display unit 22 can include an external large screen connected to the cement delivery device 16 for better display and readability.

In a particular embodiment, the control module 20 is provided by an electronic circuit board (not shown) including a microprocessor, the electronic circuit board having four objectives: (a) management of the power supply of the sensors 14, 18, 90 and the driving system 62; (b) gathering and processing signals and instructions from the sensors 14, 18, 90 and the physician; (c) advancing the syringe plunger 60 of the cement delivery device 16; and (d) outputting signals for the display unit 22. The electronic circuit board uses the external power supply 26 (see FIG. 1) for objective (a), which in the embodiments shown is a DC power supply of 24V/1.5-3 A. The control module 20 performs the other objectives.

In particular embodiments, the control module 20 has the additional objective of controlling the vacuum applied to the cannula 12a,b,c for bone fluid extraction through a vacuum regulator such as to synchronize the bone fluid extraction with the cement injection, and/or controlling the micro-motor rotating the screw delivery mechanism 43 of the cannula 12b.

In the case where a pneumatic or hydraulic cement delivery device 16 is used, the control module 20 regulates the cement delivery process through adequate proportional, differential or integral mechanisms for regulation.

In the embodiment shown, the inputs of the control module 20 include viscosity or polymerization data from the viscosity sensors 18, injection pressure data (such as injection force) from the injection pressure sensors 90 and intravertebral pressure data from the intravertebral pressure sensors 14. The signals from the sensors 14, 18, 90 can be amplified and digitized if required, for example if the sensors 14, 18, 90 generate relatively weak analog output signals.

The inputs received by the control module 20 further include a home position signal from the home position switch 104, as well as various control signals coming from the control panel 24, generated when the physician uses the command buttons, switches, knobs, etc. of the control panel 24. In a particular embodiment, the control signals are digital signals. The physician thus controls the injection process directly using the control panel 24. In a particular embodiment, the control signals from the control panel 24 include, for example, the desired cement delivery speed and volume, and commands to turn the system on, open the system to insert a syringe body, ready the plunger and syringe body for cement injection, inject the cement, reset for a different syringe body, reverse flow direction during the cement delivery, aspirate the bone marrow at a given speed, etc.

The outputs of the control module 20 include one or more actuation signals to control the driving system 62. In a particular embodiment, the actuation signals include a first signal starting/stopping the driving system 62, a second signal directing the driving system 62 to turn or translate in one of two opposed directions (e.g. clockwise or counterclockwise rotation) so that the physician can use the system to both fill and empty the syringe body 58, and a third signal providing the speed of the movement of the plunger (e.g. signal in the form of a pulse instructing the driving system 62 to move one step, the control module 20 controlling the speed and number of steps, and as such the displacement of the plunger 60, through the number and rate of the pulses). In a particular embodiment, a driver (not shown) is interposed between the control module 20 and the driving system 62 in order to implement the actuation signal(s). The driver can be in the form of hardware or alternately be programmed in the microprocessor of the circuit board providing for the control module 20.

The other outputs of the control module 20 include the data to be displayed on the display unit 22 as mentioned above (e.g. viscosity, pressures, cement delivery rate or speed, total injected volume), as well as actuation signals to the micromotor of the screw delivery mechanism 43 and/or to the vacuum system of the cannula 12a,b,c, if required.

In use and in a particular embodiment, the physician gives a command to open the device so that a syringe body can be inserted therein, for example by pressing a corresponding button on the control panel 24 to produce a corresponding control signal, preferably at the point of time of cement mixing. This causes the control module 20 to command the driving system 62 with the corresponding actuation signal(s) to move the syringe plunger 60 backwards until the home position switch 104 is activated, emitting the home position signal. Upon reception of the home position signal, the control module 20 stops the driving system 62 with the appropriate actuation signal(s), and the physician inserts the new syringe body 58. In this example the syringe body 58 is inserted in the delivery device already filled with cement, however as mentioned above the syringe body can alternately be inserted when empty and the system can be used to fill the syringe body with cement prior to injection.

When the syringe body 58 is inserted in the cement delivery device 16, the physician gives a second command to move the plunger 60 to an initial position for injection, for example by pressing a corresponding button on the control panel 24 to produce a corresponding control signal. This would typically occur soon (e.g. approximately one minute or less) after mixing of the cement. Upon reception of the control signal corresponding to the second command, the control module 20 instructs the driving system 62 to move the plunger 60 forward, for example step by step, with the corresponding actuation signal(s), until the injection pressure sensor 90 provides injection force data indicating that the plunger 60 is beginning to inject the cement from the syringe body 58. The control module 20 reads the data coming from the injection pressure sensor 90 and the other sensors 14, 18. Upon reception of the adequate injection force data, the driving system 62 is stopped by the control module 20 with the adequate actuation signal(s), and the control module 20 starts to continually send information to display on the display unit 22 and/or a computer.

After the plunger 60 is in position, the physician gives a third command to inject the cement, for example by pressing a corresponding button on the control panel 24 to produce a corresponding control signal. The physician typically gives this third command when the display unit 22 shows that the cement viscosity is appropriate. The control module 20 reads the data from the sensors 14, 18, 90, and calculates the needed injection force and the corresponding parameters (e.g. torque, speed) of the driving system 62. The control module 20 then activates the driving system 62, and as such the cement injection, through use of the corresponding actuation signal(s), in order to move the plunger 60 in a displacement-controlled, continuous manner. As well, at the same time, the control module 20 sends all the necessary information, including the data from the sensors 14, 18, 90, to the display unit 22 and/or computer. In a particular embodiment, the control module 20 only moves the driving system 62 as long as the physician gives the corresponding injection command, for example by holding a button depressed in the control panel 24, and if the command is broken (e.g. button released), the control module 20 stops the driving system 62 with the appropriate actuation signal(s) so that the injection is halted.

In a particular embodiment, the control module 20 provides pressure pulsations on the cement during delivery through actuating the driving system 62 in a pulsed manner. Pulsation enhances cement flow, and reduces the delivery pressure. An adequate mode of pulsation changes as the cement polymerizes. The pulsation mode will likely depend on the cement, and can be determined using a rheometer.

The cement delivery device 16 can also deliver haptic feedback of the intravertebral pressure to the physician. The control module 20 in this case gathers intravertebral signals, magnifies them, and sends a feedback signal to generate a contact force on the physician's hand during cement delivery, for example through a portion of the control panel 24. This feedback can be integrated in all designs.

Global Design

The cement delivery device 16 can be presented in a plurality of various exterior designs to achieve the present invention, any one of which can include and enclose any one of the mechanisms shown in FIGS. 8-10, a combination thereof, or any other appropriate mechanism transmitting power from the driving 62 to the syringe plunger 60.

Figure 20:
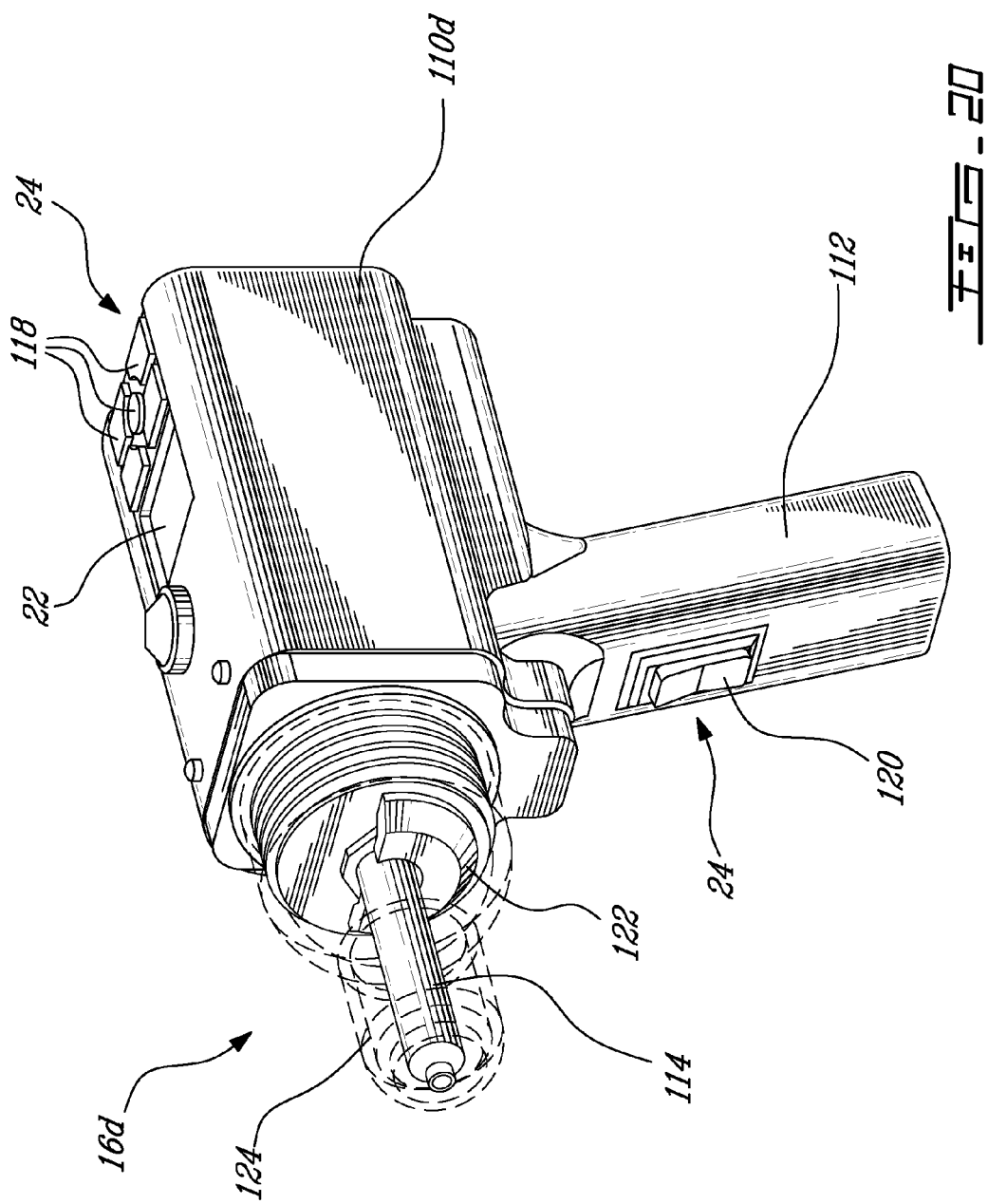
FIG. 20 is a tridimensional view of a cement delivery device according to a particular embodiment of the present invention.

FIG. 20 illustrates a particular embodiment 16d of the cement delivery device 16, which is in the shape of a cement gun and is simple and portable. The device 16d comprises three principle parts: a body 110d, a handle 112, and a syringe 114. The body 110d includes on a top face thereof the display unit 22, for example in the form of a LCD display screen, and command buttons 118 forming part of the control panel 24 to ensure easy access and utilization, the command buttons 118 allowing the physician to generate the control signals described above and shown in FIG. 19. The device 16d is operated by the handle 112, which is solidly attached to the body 110d. The handle 112 includes a command button 120 on the front thereof to control the cement injection, forming a second part of the control panel 24. In a particular embodiment, the command button 120 allows the physician to give the third or injection command described above.

Once the syringe 114 is filled with cement, it is positioned in a cylindrical cavity defined in a block 122 which is part of the body 110d. The device 16d also includes a translucent syringe support 124 that is screwed into the block 122. This stabilized the syringe 114 and eases the injection.

Figure 21:
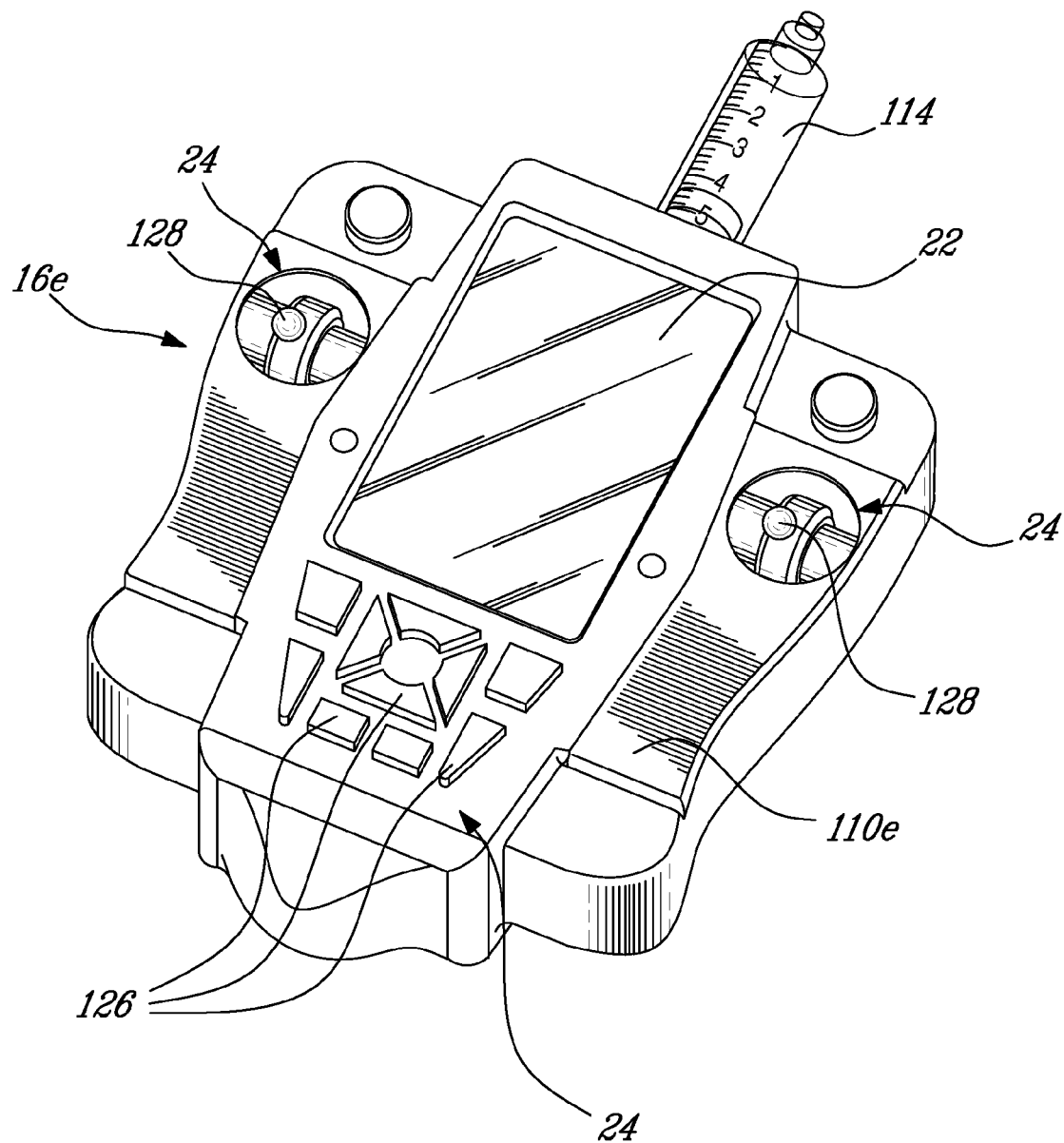
FIG. 21 is a tridimensional view of a cement delivery device according to an alternate embodiment of the present invention.

FIG. 21 illustrates another particular embodiment 16e of the cement delivery device 16, which is a portable apparatus comprising two principle parts: a body 110c and a syringe 114. The body 110e provides an easy to use and consistent interface, including the display unit 22, for example in the form of a large LCD display, and command buttons 126 defining part of the control panel 24 and located directly underneath the display unit 22 for easy access. In a particular embodiment, the command buttons 126 allow the physician to generate some of the control signals described above and shown in FIG. 19. The body 110e also includes two flexible levers 128 placed on opposite sides of the display unit 22 and forming another part of the control panel 24, to allow the physician to provide others of the control signals described above, such as for example the desired injection volume and speed of the cement. The body 110e is curved on both sides to allow for comfortable hand control of the levers 128.

Figure 22:
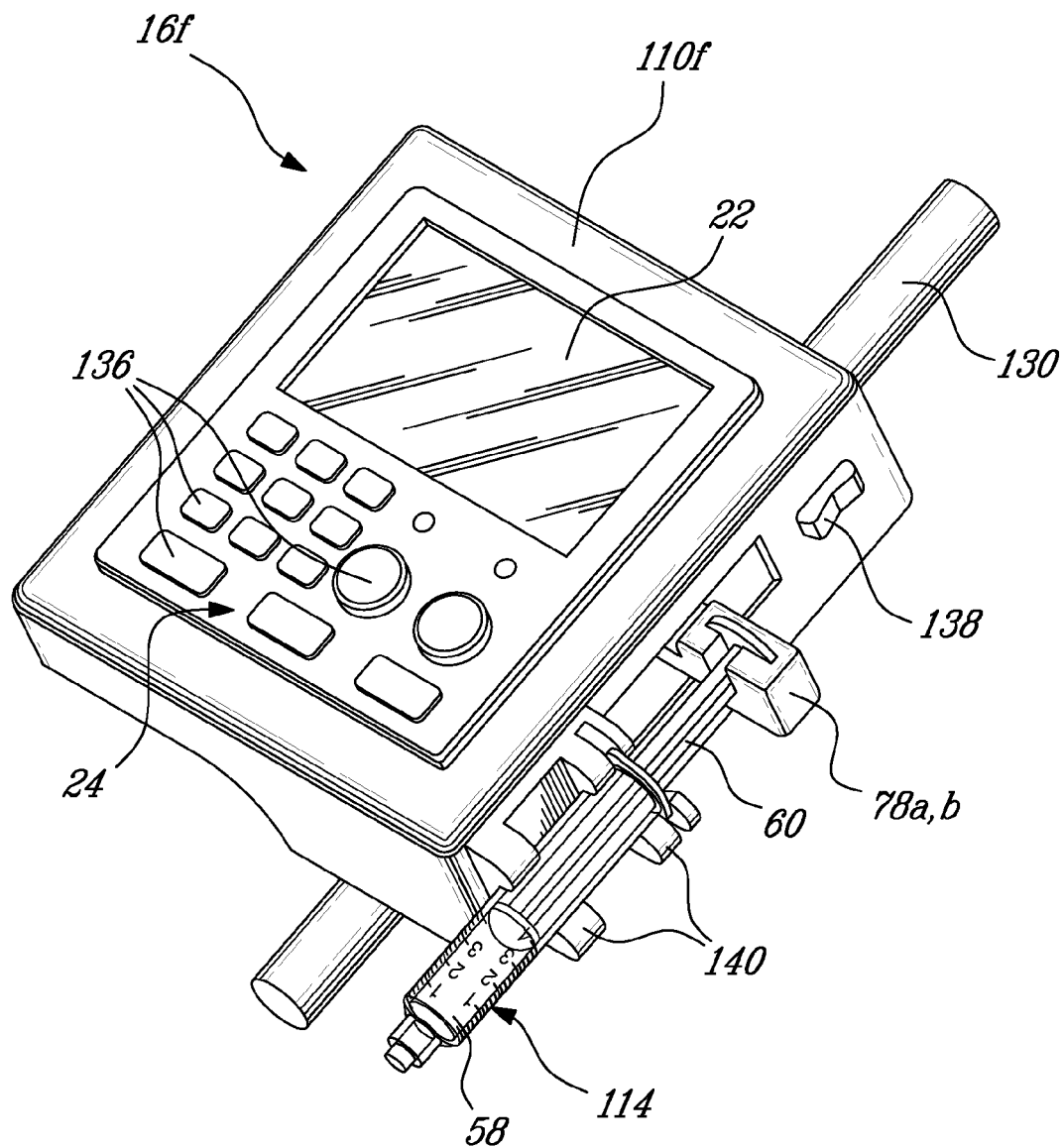
FIG. 22 is a tridimensional view of a cement delivery device according to an alternate embodiment of the present invention.

FIG. 22 illustrates another particular embodiment 16f of the cement delivery device 16, which is also simple and easy to use. The device 16f is vertically attached to a fixing bar 130, for example by surrounding fastener tightened by a screw, allowing the position of the device 16f to be easily adjusted on the bar 130.

The device 16f comprises three principle parts: a body 110f, the fixing bar 130, and a syringe 114. The body 110f includes on a side thereof a syringe support 140 that secures the syringe 114 once it is filled with cement. A pushrod such as shown for example at 78a,b in FIGS. 8-9 protrudes from the body 110f and engages the plunger 60 of the syringe 114, such that the movement to the pushrod 78a,b activates the plunger 60 which moves inside the syringe body 58 to force the injection of the cement.

The device 16f includes the display unit 22 on a front face of the body 110f, for example in the form of a large LCD display, thus improving visibility and access to the results. The control panel 24 is in the form of command buttons 136 placed underneath the display unit 22 where they are easily accessible. In a particular embodiment, the command buttons 136 allow the physician to generate the control signals described above and shown in FIG. 19. The body 110f further includes, on a side thereof, a button 138 to control a light.

Figure 23:
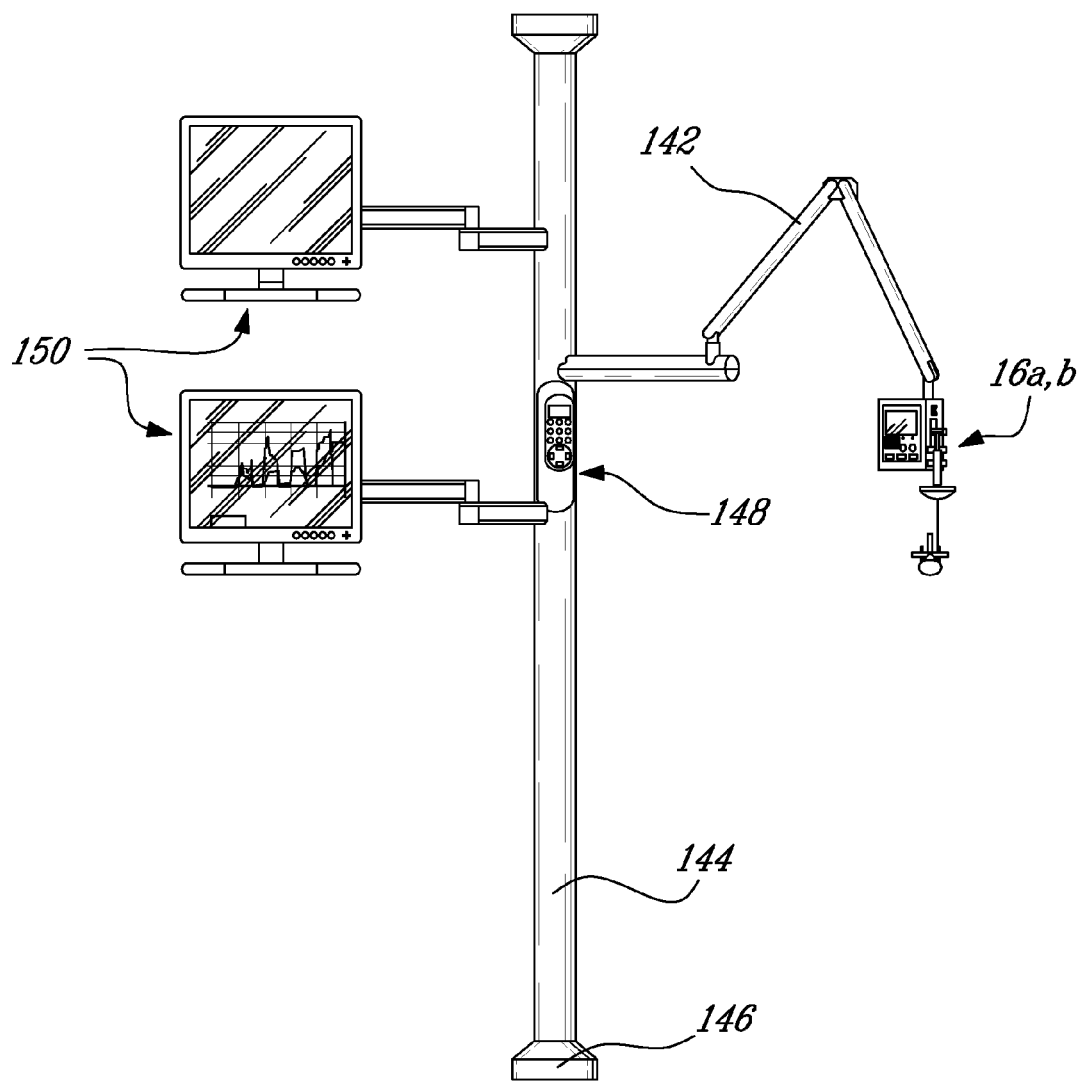
FIG. 23 is a tridimensional view of a cement delivery system according to a particular embodiment of the present invention, shown here in combination with the cement delivery device depicted in FIG. 22.

FIG. 23 shows a design for the cement delivery system 10 according to a particular embodiment which allows reduced x-rays exposure for the physician. The device 16f of FIG. 22 is shown supported by a flexible arm 142 which is attached to an upright post 144 extending from a base 146. Also supported on the post in an auxiliary control panel 148 allowing remote control of the position of the arm 142 and/or the same controls/commands provided by the control panel 24. Further supported on the post are auxiliary display units 150 providing a larger, easier to read display for the information displayed on the display unit 22 and/or any additional pertinent information, such as fluoroscopic visualization data. It is understood that the configuration of FIG. 23 can alternately be used with any other appropriate design for the cement delivery device 16.

The elements of the cement delivery device 10 thus help improve bone cement injection procedures, such as vertebroplasty. The displacement controlled cement delivery device 16a,b,c advantageously provides for a continuous, slow and precise cement delivery, with an injection pressure exceeding pressures that can be manually applied, thus allowing for thicker cement to be delivered. The viscosity sensors 18 provide for real time, in-situ monitoring of the cement curing, within the syringe body 58, thus allowing for the cement to be injected at its optimum viscosity. The cannulae 12a,b,c allow for bone marrow aspiration simultaneously with bone cement injection, which guides the bone cement within the bone as well as reduces the risks of emboli. The cannulae 12a,b,c with an intervertebral or other inner bone pressure sensor 14, either connected to a cannula conduit or embedded in the cannula itself, allow for monitoring of the intravertebral pressure, to ensure that there is no excess pressure within the bone, as well as for providing an indication that cement leakage is about to occur or is starting when a sudden drop of pressure is detected. The syringe equipped with a pressure sensor 90 allows for the determination of the injection pressure, which provides information on the pressure drop within the cannula and as such on the viscosity of the bone cement. Any one of these elements can be integrated in a typical cement delivery system, or alternately be combined with any one, any group of, or all of the others.

In a particular embodiment, the cement delivery system 10 is an integrated cement delivery system and includes the displacement-controlled cement delivery device 16a,b,c, the pressure sensors 14 and/or 90, the viscosity sensors 18, and the control system 102 including the control module 20, the display unit 22 and the control panel 24. This integrated system advantageously improves the safety and predictability of cement delivery, by providing warnings when the pressure is out of normal ranges, controlling the delivery of bone cement, and insuring that the cement has an appropriate viscosity on delivery to minimize the risk of leakage.

The cement delivery system 10 of the present invention allows the physician to control cement delivery by deciding on the injection rate and mode, total injection volume, and period of cement delivery. If required, the physician can adjust and overwrite the settings of the system 10.

The rod 70c is detachably connected to the head 88 or piston in the syringe. As the rod 70c advances it moves the piston against the cement. If for some reason the physician wishes to reduce the pressure applied to the cement he/she may press the button to stop the advance of the rod 70c. At the same time the direction of the movement of the rod may be reversed, for example approximately 0.1 mm in order to reduce the pressure on the cement. Since the rod is attached to the piston, it will be moved backwards as well. This way the same delivery mechanism can be used for depressurization.

The cement delivery system 10 described herein provides the advantage of concomitantly overcoming the limitation of excessive pressure and providing assistance to enhancing filling uniformity such as to reduce the risk of cement leakage. Additionally, the cost effective system 10 can be simply incorporated into the vertebroplasty procedure without substantially affecting or changing how the procedure is performed. Another advantage is that it provides physicians with real time monitoring of the cement delivery process, which is vital to guiding the intravertebral flow and preventing leakage, instead of reacting to visual fluoroscopic clues once leakage has occurred. Thus, the cement delivery system 10 allows the physician to prevent, or at least reduce the risk of, leakage rather than detecting it.

The system 10 also allows the guiding of the intravertebral cement filling during cement delivery, for example with the cannulae 12a,b,c, thereby enhancing filling uniformity and reducing leakage risk. Flow guidance is also improved by delivering cement of adequate viscosity. The miniature viscosity sensors 18 provide constant readings of polymerizing cement viscosity such as to inject cement having an optimal viscosity.

The system 10 ensures slow and continuous cement delivery, thereby leading to low intravertebral pressure and enhancing smoothness and precision of delivery. Accurate cement delivery and low pressure reduces leakage risk. More explicitly, precise delivery ensures exact filling volume, thereby reducing undesired excess cement which increases leakage risk. Continuous delivery results in steady flow, thereby reducing undesired transient peaks in pressure which augment leakage risk. Displacement-controlled delivery leads to stable cement flow conditions, thereby reducing the risk of sudden uncontrolled flow, which is difficult to monitor under fluoroscopy. Delivery forces of at least 2 KN reduce the risk of insufficient filling when delivering thick cement. With live monitoring of pressures and viscosity during procedures, physicians are alerted by acoustic or visual signals when polymerizing cement attains adequate viscosity of safe delivery. With this strengthening tool, physicians are alerted when delivery results in high unsafe pressures. Finally, with slow cement delivery, the physician has sufficient time to monitor intravertebral filling and if necessary to intervene, thereby preventing further leakage. The extended time of monitoring and reaction combined with fluoroscopic visualization enhance procedural safety.

The system 10, through the designs shown for the devices 16d,e,f, is ergonomically designed. The cement delivery device 16 is light and in a particular embodiment weighs approximately 0.5 kg. Physicians interact with it in a simple manner. The system 10 is also economical in design, with the main components being reusable. Disposable items are specialized syringes and cannulae, which can be bundled in a set.

The system 10 resulted from a thorough biomechanical understanding of the cement delivery process and forces governing the intravertebral flow in vertebroplasty. The system 10 and currently used fluoroscopic visualization can advantageously complete each other by attacking the problem from two different, yet, complimentary angles, the system 10 allowing a substantial reduction in the risk of leakage while the fluoroscopic visualization allowing the detection of leakage if leakage does occur. Thus, when combined together the two methods can provide a safer and more reliable vertebroplasty procedure, assisting the physician in foreseeing and preventing cement leakage.

In another embodiment, the cannula may be provided with a collar on the exterior wall to serve as a stopper which would limit the penetration of the cannula in the pedicle. In a particular embodiment, the collar is a simple annular ring surrounding the exterior wall, spaced apart from the proximal end.

The invention claimed is:

1. A bone cement delivery system for vertebroplasty comprising a rigid cannula having:
   a tubular inner wall defining and surrounding a central conduit to deliver bone cement into a vertebra under pressure, the inner wall defining a distal outlet port of the central conduit at a distal end of the cannula;
   a tubular outer wall extending around the inner wall and spaced apart therefrom to define a peripheral conduit around the central conduit for aspirating bone fluids, the outer wall defining a plurality of fenestrations defined at the distal end, the outer wall defining a distal inlet port of the peripheral conduit at the distal end of the cannula;
   the outer wall having an outer diameter not exceeding acceptable parameters for vertebroplasty;
   a proximal end of the cannula including a proximal inlet port in communication with the central conduit and a proximal outlet port in communication with the peripheral conduit;
   a vacuum pump communicating with the proximal outlet port of the peripheral conduit to create a pressure gradient between the central conduit and the peripheral conduit to provide a hydraulic force guiding the displacement of bone fluid and the flow of cement;
   a source of bone cement delivering bone cement to the proximal inlet port; and
   a helical thread defining a screw delivery mechanism in the central conduit extending from the proximal inlet port to the distal outlet port.

2. The bone cement delivery system according to claim 1, further including a pressure sensor connected to the proximal outlet port such as to sense an internal pressure at the distal inlet through the peripheral conduit.

3. The bone cement delivery system according to claim 1, wherein the screw delivery mechanism includes an inner conduit defined therewithin and along a length thereof, the inner conduit being concentric with the central conduit.

4. The bone cement delivery system according to claim 3, further including a pressure sensor connected to a proximal outlet of the inner conduit such as to sense an internal pressure at the distal end of the cannula through the inner conduit.

5. The bone cement delivery system as defined in claim 1, wherein the vacuum applied is in the range of 10 to 100 KPa.

6. The bone delivery cement system as defined in claim 1, wherein the outlet port of the central conduit and the inlet port of the peripheral conduit are spaced apart linearly.

7. The bone cement delivery system as defined in claim 1, further including an elastic and permeable membrane covering the distal outlet port of the central conduit for delivery of injected fluid therethrough.

8. The bone cement delivery system according to claim 7, wherein the cannula is used to deliver bone cement, and the membrane has a permeability.

9. The bone cement delivery system according to claim 8, wherein the size and elasticity of the membrane is such as to define an expanded diameter of at most 5 mm.

* * * * *